United States Patent [19]
Yeo

[11] Patent Number: 5,509,913
[45] Date of Patent: Apr. 23, 1996

[54] FLUSHABLE COMPOSITIONS

[75] Inventor: Richard S. Yeo, Dunwoody, Ga.

[73] Assignee: Kimberly-Clark Corporation, Neenah, Wis.

[21] Appl. No.: 516,967

[22] Filed: Aug. 18, 1995

Related U.S. Application Data

[63] Continuation of Ser. No. 386,247, Feb. 9, 1995, abandoned, which is a continuation of Ser. No. 168,807, Dec. 16, 1993, abandoned.

[51] Int. Cl.$^6$ .............................. A61F 13/15; A61F 13/20
[52] U.S. Cl. ..................... 604/364; 604/358; 604/367; 604/374; 604/375; 604/372; 525/329.7; 525/330.2
[58] Field of Search ............................ 525/330.2, 329.7; 604/358, 364–365, 367–368, 372, 374–375, 385.1

[56] References Cited

U.S. PATENT DOCUMENTS

| | | |
|---|---|---|
| 2,948,697 | 8/1960 | Robertson . |
| 3,157,611 | 11/1964 | Lindemann . |
| 3,510,587 | 5/1970 | Marder et al. . |
| 3,554,788 | 1/1971 | Fechillas . |
| 3,559,650 | 2/1971 | Larson . |
| 3,580,253 | 5/1971 | Bernardin .................. 604/375 |
| 3,606,887 | 9/1971 | Roeder . |
| 3,635,221 | 1/1972 | Champaigne, Jr. ............ 604/364 |
| 3,654,928 | 4/1972 | Duchane .................... 604/375 |
| 3,686,024 | 8/1972 | Nankee et al. ............... 604/368 |
| 3,692,725 | 9/1972 | Duchane . |
| 3,800,797 | 4/1974 | Tunc ....................... 604/374 |
| 3,804,092 | 4/1974 | Tunc . |
| 3,808,165 | 4/1974 | Duchane . |
| 3,881,210 | 5/1975 | Drach et al. . |
| 3,886,112 | 5/1975 | Watson et al. . |
| 3,892,905 | 7/1975 | Albert . |
| 3,897,782 | 8/1975 | Tunc . |
| 3,923,592 | 12/1975 | George et al. . |

(List continued on next page.)

FOREIGN PATENT DOCUMENTS

| | | |
|---|---|---|
| 948802 | 6/1974 | Canada . |
| 1104026 | 6/1981 | Canada . |
| 1109758 | 9/1981 | Canada . |
| 1171579 | 7/1984 | Canada . |
| 1190014 | 7/1985 | Canada . |
| 0143935 | 6/1985 | European Pat. Off. . |
| 0388924 | 9/1990 | European Pat. Off. . |
| 0569699A1 | 11/1993 | European Pat. Off. . |
| 2-082925 | 9/1988 | Japan . |
| 3-027195 | 6/1989 | Japan . |
| 1452325 | 10/1976 | United Kingdom . |
| 2048078 | 12/1980 | United Kingdom . |
| 2193925 | 2/1988 | United Kingdom . |
| 90/03156 | 4/1990 | WIPO . |
| 91/14413 | 10/1991 | WIPO . |
| WO92/02199 | 2/1992 | WIPO . |
| 92/15742 | 9/1992 | WIPO . |
| 92/18079 | 10/1992 | WIPO . |
| 9309740 | 5/1993 | WIPO ................. 604/378 |

OTHER PUBLICATIONS

WPI Abstract Accession No. 93-303509/37 and JP 4208162A (Unitika Ltd) Jul. 29, 1992 (See Abstract).
WPI Abstract Accession No. 92-038939/05 and JP 3286727A (Nippon) Dec. 17, 1991 (See Abstract).

(List continued on next page.)

*Primary Examiner*—Randall L. Green
*Assistant Examiner*—P. Zuttarelli
*Attorney, Agent, or Firm*—Patrick C. Wilson

[57] ABSTRACT

The present invention encompasses flushable compositions and flushable products, such as flushable personal hygiene articles, flushable medical, hospital and surgical supplies, and flushable household wipes and packaging material that have sufficient wet tensile strength for their intended use, particularly prolonged or extended use, in the presence of body waste fluids, but which disintegrate and disperse in the presence of ordinary tap water so as to be flushable in a conventional toilet and disposable in municipal or private sewage systems without obstructing or clogging the toilet or sewage system.

19 Claims, 17 Drawing Sheets

U.S. PATENT DOCUMENTS

| | | | |
|---|---|---|---|
| 3,939,836 | 2/1976 | Tunc . | |
| 3,950,578 | 4/1976 | Laumann . | |
| 4,005,251 | 1/1977 | Tunc . | |
| 4,009,313 | 2/1977 | Crawford et al. . | |
| 4,033,918 | 7/1977 | Hauber . | |
| 4,117,187 | 9/1978 | Adams et al. . | |
| 4,186,233 | 1/1980 | Krajewski et al. . | |
| 4,245,744 | 1/1981 | Daniels et al. . | |
| 4,258,849 | 3/1981 | Miller . | |
| 4,309,469 | 1/1982 | Varona . | |
| 4,327,447 | 5/1982 | Carnaghi et al. . | |
| 4,340,563 | 7/1982 | Appel et al. . | |
| 4,343,403 | 8/1982 | Daniels et al. . | |
| 4,347,092 | 8/1982 | Hlaban et al. . | |
| 4,362,781 | 12/1982 | Anderson . | |
| 4,372,447 | 2/1983 | Miller . | |
| 4,419,403 | 12/1983 | Varona . | |
| 4,469,728 | 9/1984 | Belz . | |
| 4,522,967 | 6/1985 | Sheldon et al. . | |
| 4,537,807 | 9/1985 | Chan et al. . | |
| 4,551,369 | 11/1985 | Belz . | |
| 4,612,355 | 9/1986 | Belz . | |
| 4,619,862 | 10/1986 | Sokolowski et al. . | |
| 4,671,982 | 6/1987 | Belz . | |
| 4,676,773 | 6/1987 | Sheldon . | |
| 4,704,116 | 11/1987 | Enloe . | |
| 4,734,941 | 4/1988 | DeWitt et al. . | |
| 4,762,738 | 8/1988 | Keyes et al. . | |
| 4,798,603 | 1/1989 | Meyer et al. . | |
| 4,830,187 | 5/1989 | Keyes et al. . | |
| 4,868,024 | 9/1989 | Cross et al. . | |
| 4,870,148 | 9/1989 | Belz et al. . | |
| 4,930,942 | 6/1990 | Keyes et al. . | |
| 4,938,757 | 7/1990 | Van Gompel . | |
| 4,940,464 | 7/1990 | Van Gompel . | |
| 4,944,735 | 7/1990 | Mokry . | |
| 4,964,857 | 10/1990 | Osborn . | |
| 5,002,526 | 3/1991 | Herring . | |
| 5,026,363 | 6/1991 | Pratt . | |
| 5,032,121 | 7/1991 | Mokry . | |
| 5,041,252 | 8/1991 | Fujii et al. . | |
| 5,063,272 | 11/1991 | Sasse . | |
| 5,084,553 | 1/1992 | Hess et al. . | |
| 5,089,535 | 2/1992 | Malwitz et al. . | |
| 5,192,606 | 3/1993 | Proxmire et al. . | |
| 5,312,883 | 5/1994 | Komatsu et al. | 526/318.44 |
| 5,317,063 | 5/1994 | Komatsu et al. | 525/330.2 |

OTHER PUBLICATIONS

WPI Abstract Accession No. 89–285647/39 and ZA 8802776A (Carlton Paper) Dec. 28, 1988 (See Abstract).

Search Report, Application No. GB 9425378.8, 23 Mar. 1995.

Search Report, Application No. PCT/US 94/14034, 31 Mar. 1995.

"Effect of Additivies on Solution Properties of Ethylene Oxide–Propylene Oxide Statistical Copolymers", Polymer, 1991, vol. 32 No. 4, pp. 713–720.

"Solubility and Miscibility of Poly(ethyl oxazoline)", Journal of *Polymer Science: Part B: Polymer Physics*, vol. 26, No. 3, pp. 603–619 (1988).

"Phase Diagrams of Nonionic Polymer–Water Systems" by G. Karlstrom, A. Carlsson, B. Lindman, Journal of Physical Chemistry vol. 94, pp. 5005–5015 (1990).

"Effect of Electrolytes on Solution Behavior of Water Soluble Macromolecules" by M. J. Garvey and I. D. Robb, *Journal of Chemistry Society*, Faraday Transactions I. vol. 75, pp. 993–1000 (1979).

"Studies on Sol–Gel Transformations. I. The Inverse sol–gel Transformation of Methyl Cellulose In Water" by Heymann *Transaction of the Faraday Society*, vol. 94, pp. 846–864 (1935).

"Vinyl Ether Monomers and Polymers" by E. V. Hort and R. C. Gasman, *Enclyclopedia of Chemical Technology*, Vo. 23, pp. 937–960, 3rd. Ed. John Wiley and Sons, New York.

"Water Solubility and Sensitivity–Hydration Effects" by F. Frans Chemistry and Technology of Water–Soluble Polymers, ed. by C. A. Finch, Plenum Press, New York (1983) pp. 157–178.

"Some Properties of Poly(ethylene oxide) In Aqueous Solution" by F. E. Bailey and R. W. Callard, *Journal of Applied Science*, vol. 1, Issue No. 1, pp. 56–62 (1959).

Hammons, J. L. et al., "Compositional Variations in Human Urine and Influences on Urinary Absorbent Products Testing" 1987 TAPPI Proceedings, International Dissolving Pulps Conference pp. 247–264 (1987).

Pinner S. H., et al., "Gelation of Polymethacrylic Acid Solutions with Monovalent Salts", pp. 478–480 (1952).

Ikegami, A. et al., "Precipitation of Polyelectrolytes by Salts" Journal of Polymer Science, vol. 56, pp. 133–152 (1962).

Wall, F. T., et al., "Gelation of Polyacrylic Acid by Divalent Cations" vol. VII, No. 1, pp. 83–88 (1951).

Lindemann, M. K. et al., "Vinyl Alcohol Polymers", Encyclopedia of Polymer Science and Engineering, vol. 17, pp. 167–198.

Koltisko, B. M., "Binders for Flushable Nonwovens," INDA Idea90 Conference, Sep. 1990, Washington D.C. (1990).

Brochure entitled, "KLUCEL Hydroxypropylcellulose, Physical and Chemical Properties," by Aqualon (Jan. 1988).

FLUSHABLE COMPOSITIONS

This application is a continuation of application Ser. No. 08/386,247 entitled "FLUSHABLE COMPOSITIONS" and filed in the U.S. Patent and Trademark Office on Feb. 9, 1995, now abandoned, and which is a continuation of application Ser. No. 08/168,807 entitled "FLUSHABLE COMPOSITIONS" and filed in the U.S. Patent and Trademark Office on Dec. 16, 1993, now abandoned.

FIELD OF THE INVENTION

The present invention relates to products that may be disposed of by flushing in a conventional toilet. More particularly, the present invention encompasses flushable personal hygiene products and flushable medical, surgical and hospital products that are reversibly water insoluble so as to retain their integrity in the presence of body waste fluids, but which disintegrate and disperse in the presence of normal tap water.

BACKGROUND OF THE INVENTION

Disposable products have revolutionized modern lifestyle and are of great convenience to society. Such products generally are relatively inexpensive, sanitary and quick and easy to use. Disposal of such products, however, increasingly is a problem as landfills close and incineration contributes to urban smog and pollution. Consequently there is an urgent need for disposable products that can be disposed of without dumping or incineration. An ideal disposal alternative would be the use of municipal sewage treatment and private residential septic systems. Products suited for disposal in sewage systems that can be flushed down a conventional toilet are termed "flushable." An essential feature of flushable products is that they must have sufficient wet strength for their intended use, yet lose structural integrity upon contact with water. Meeting these dual criteria is particularly difficult for products that come in contact with body waste fluids, especially urine, due to their similarity to normal tap water, as illustrated in Table 1.

TABLE I

| Parameter | Infant Urine | Tap Water |
|---|---|---|
| pH | 5.8–8.5 | 5.0–10.5 |
| Calcium | 4–182 ppm | 0–145 ppm |
| Magnesium | 6–333 ppm | 0–120 ppm |
| Sodium | 12–6,200 ppm | 1–198 ppm |
| Chloride | 190–10,320 ppm | 0–540 ppm |
| Sulfate | 23–3,514 ppm | 0–572 ppm |

A distinct difference between urine and normal tap water is temperature. The skin temperature within the area enclosed by a disposable diaper is shown in Table 2 (cited from "Factors influencing infant diaper dermatitis" by W. E. Jordan and T. L. Blaney, published in *Neonatal Skin*, edited by H. Maibach and E. K. Boisits, Marcel Dekker, Inc., New York, 1982.).

TABLE 2

Skin Temperature Within the Diapered Area (Disposable Diaper)

| Site | Skin temperature[a] (°F.) | (°C.) |
|---|---|---|
| Diapered area | | |
| Pubic | 95.3 | 35.2 |
| Intertriginous | 97.9 | 36.6 |
| Buttocks | 89.4 | 31.9 |
| Normally exposed skin | | |
| Abdomen | 95.5 | 35.3 |
| Outer aspect of thigh | 90.6 | 32.6 |

[a]Study base = 25 infants

Toilet bowl water temperature initially is determined by the temperature of tap water and subsequently approaches room temperature (20° C. to 25° C.) with time. Tap water temperature is effected by the temperatures of ground water and surface water which make up the tap water, as well as ambient room temperature. After toilet bowl water is discharged into the sewage system, the water temperature drops as it moves underground.

The normal temperature of ground water at shallow depths in the United States ranges from a low of about 3° C. to a high of 25° C. The temperature of shallow ground water in a particular locality is determined mainly by the mean annual air temperature of the region. At greater depths, the internal heat of the earth controls the temperature, which on the average, increases approximately one degree Fahrenheit with each additional 50 to 100 feet of depth below land surface. Normal ground water temperatures at a depth of 30 to 60 feet seldom vary more than a degree or so all year long, and at greater depths, remain practically unchanged. The lowest ground-water temperatures (3° C.) are in northern Minnesota and the highest temperatures (25° C.) are in the extreme southern tip of Florida. In the eastern part of the country, ground water temperatures show a more or less regular increase from north to south. Table 3 shows the percent area of the United States that has shallow ground water at a particular temperature range.

TABLE 3

| Temperature above | | |
|---|---|---|
| (°F.) | (°C.) | %, area |
| 77 | 25.0 | 0.1 |
| 72 | 22.2 | 3.2 |
| 67 | 19.4 | 14 |
| 62 | 16.7 | 27 |
| 57 | 13.9 | 40 |
| 52 | 11.1 | 59 |
| 47 | 8.3 | 79 |
| 42 | 5.6 | 95 |
| 37 | 2.8 | 100 |

The temperature of surface water (lakes, rivers and reservoirs) varies with geographic location and season. In July/August, the highest surface water temperatures (32° C.) are in the south-western part of Arizona and extreme southeastern parts of California. Table 4 shows the percent area of United States that has surface water at a particular temperature range in July/August.

TABLE 4

| Temperature | | % of area of United States having surface water temperature |
|---|---|---|
| (°F.) | (°C.) | above the indicated temperature |
| 90 | 32 | 1 |
| 85 | 29 | 3 |
| 80 | 27 | 24 |
| 75 | 24 | 45 |
| 70 | 21 | 69 |
| 65 | 18 | 92 |
| 60 | 16 | 99 |
| 50 | 10 | 100 |

It is obvious from this data that only less than 3% of the country and less than two months of the year have surface water temperature above 29° C.

Numerous attempts have been made to produce flushable fibers, fabrics, films and adhesives that retain their integrity and wet strength in the presence of body waste fluids, yet can be disposed of via flushing in conventional toilets. One approach to producing a flushable product is to limit the size of the product so that it will readily pass through plumbing without causing obstructions or blockages. Such products have high wet strength and do not disintegrate during flushing. Examples of this type of product include wipes such as baby wipes. This approach to flushability suffers the disadvantage, however, of being restricted to small sized articles. Many of the current flushable products are limited to such small articles.

Another approach to producing a flushable product is to manufacture a product that is normally insoluble in water, but which disintegrates in the presence of alkaline or acidic aqueous solutions. The end user is provided with an alkaline or acidic material to add to the water in which the product is to be disposed. This approach permits disposal via normal plumbing systems of products substantially larger than wipes, but suffers from the disadvantage of requiring the user to perform the step of adding the dissolving chemical to the water. A further disadvantage is that the inadvertent or intentional disposal of such a product in a conventional toilet without the addition of the dissolving chemical can cause serious obstruction of blockage of the plumbing system. The latter disadvantage can, however, be overcome by incorporating the dissolving acid or alkali into the article but separate from the dissolvable material while in use. The dissolving chemical is only released upon contact with water during flushing.

Similarly, another approach to producing a flushable product, particularly wipes, consists of forming the product from a pH sensitive gelled polymer and storing the product in the presence of a separate acid pH solution. When the wipe is placed in a large quantity of neutral pH water, it disintegrates as a result of the pH shift. A disadvantage of this pH shift approach to flushability is that some acidic polymers lose wet strength at slightly alkaline pH in the range of 7–8. Because the pH of urine may be as high as 8.5, these flushable materials are not well suited for use in, for example, diapers or incontinence pads.

Another approach to producing a flushable product is to combine water soluble material with water insoluble material to form a mixed material product. Upon contact with water, the water soluble material dissolves, reducing the structural integrity of the article, and causing its disintegration, such that it will easily pass through the plumbing system. A similar approach is to blend together a water insoluble material with a water soluble material such that the water insoluble material retards the contact of water with the water soluble material.

Yet another approach to producing a flushable product is to form the product from material that is susceptible to attack by specific enzyme catalysis that breaks down the structural integrity of the material. In such a product the enzymes may be introduced into the disposal water separately. These systems suffer many of the same disadvantages as those described above for alkaline or acid treatable materials. Still another approach to producing a flushable product is to use polyvinyl alcohol polymers, or copolymers wherein one polymer is polyvinyl alcohol, which gel in the presence of borate ions in aqueous solution, but which break down in the presence of large excesses of water as the borate ion diffuses away from the polymer and the borate ion concentration decreases. A major disadvantage of these flushable products is that they must be pre-moistened, and thus, are limited to articles such as pre-moistened wipes. Additionally, the high concentration of boric acid required, while suitable for products that contact the skin only temporarily, may cause irritation upon prolonged contact with skin if used, for example in a diaper or incontinence pad intended to be worn for extended period of time. Furthermore, these polymers when dry are not suitable for use in products such as diapers and incontinence pads because the salt concentration in urine often will be too low to ensure insolubility of the product while in use. Products made of these materials would dissolve during use in the absence of added salt.

Wipes have been made using colloidal cellulose sulfate esters as binders. The colloidal cellulose sulfate esters form aqueous gels in the presence of potassium ions. The immersion in water of such wipes results in the gel breaking and the wipe dispersing.

Still others have attempted to make flushable products wherein a non-woven web is bound together with salt-sensitive binders. For example, some acrylic copolymers precipitate in the presence of high concentrations of calcium ions. The problem with calcium-dependent water soluble binders, however, is that across the country the concentration of calcium in normal tap water varies tremendously. Consequently, flushable products made with those binders may not, in fact, be flushable in regions with high calcium containing water. Water analyses of metropolitan Los Angeles water supplies demonstrate the wide variations that can occur. See, 1982–1983 Analyses of Metropolitan's Water Supplies. For example, one water source had 83 mg/L of calcium whereas another water source had only 16 mg/L of calcium. Similar variances were found for other ions as well, as illustrated by the specific conductance measurements, which ranged from 252 μmho/cm to 1106 μmho/cm.

Not only does the ionic and pH character of normal tap water vary tremendously in different geographic locales, but the salt concentration of body waste fluids, especially urine, varies greatly at different times during the day and under different conditions. Compositional differences in dietary intake lead to tremendous variations in the urinary output of electrolytes. For example, the urinary concentrations of sodium, potassium, chloride, phosphate and urea are lower in breast-fed infants than formula-fed infants. Furthermore the amount of intake affects urine electrolyte composition as more fluid is taken in the concentration of urinary salts decreases. Salt variations in a normal diurnal period can fluctuate ±40% from the 24 hour mean concentrations. As a consequence of these variations, prior art flushable compositions often are not suited for all disposable products, especially diapers and incontinence pads.

In the prior art, precipitating salts generally are supplied to the local external environment around the polymeric material. An example is personal care pre-moistened wipes, where precipitating salts are dissolved in the solution surrounding the wipe. This method of introducing salt to a flushable material is impossible, however, when the flushable article is provided dry, such as with flushable diapers. Alternatively, salts or other additives may be coated on the external surface of flushable materials. The latter method prevents the salt or additive from quickly washing in the presence of small amounts of water such as perspiration, but provides only a limited functional time for using the flushable article after contact with bodily fluids or wastes, unless excess salt or additive is provided to counteract these effects. The high concentrations of salt or additives required to ensure structural integrity during use, in turn may cause undue irritation to the wearer of the flushable article. What is needed are flushable products having sufficient wet strength for their intended use, which contain polymers that can be made reversibly insoluble in the presence of body waste fluids, but soluble in normal tap water, and therefore flushable in conventional toilets.

SUMMARY OF THE INVENTION

It is, therefore, an object of the present invention to provide disposable products that can be flushed in a conventional toilet.

It is a further object of the present invention to provide disposable products that can be flushed in a conventional toilet without the addition of a dissolving chemical.

It is yet another object of the present invention to provide flushable products that are reversibly water insoluble in the presence of body waste fluids, but which are water soluble in the presence of normal tap water.

It is a further object of the present invention to provide flushable products that dissolve or disintegrate and disperse in normal tap water regardless of geographic variations in tap water salt concentrations.

It is still another object of the present invention to provide flushable products that have sufficient wet strength for their intended use.

Yet another object of the present invention is to provide flushable binders, flushable fibers, flushable fabrics, flushable films, flushable elastomeric yarns, flushable tapes, flushable adhesives, and flushable foams.

Still another object of the present invention is to provide flushable personal hygiene products, flushable medical, hospital, surgical supplies, disposable household wipes, and disposable packaging material.

The present invention encompasses flushable products that have sufficient wet strength for their intended use, particularly prolonged or extended use, in the presence of body fluids and at temperatures above 25° C., but which disintegrate and disperse in the presence of ordinary tap water. More particularly, the flushable articles of the present invention contain one or more temperature sensitive polymers that are reversibly water insoluble under certain conditions. Temperature sensitive polymers may be combined with salts, such that the salt is admixed into the bulk of the polymer, to modulate the temperature at which the resulting composition is soluble in water. The anion of the salt influences the temperature at which the composition becomes water soluble. The effectiveness of some common anions is as follows $PO_4^{3-} > SO_4^{2-} > CO_3^{2-} > Cl^- > Br^-$.

Desirable embodiments include polyvinyl methyl ether, polyethyl oxazoline, polyvinyl pyrrolidone, hydroxy propyl cellulose and polyvinyl alcohol having a percent hydrolysis of less than approximately 75% combination with an anion of a salt, such as disodium hydrogen phosphate, or another salt selected from the group consisting of sulfate salts, citrate salts, phosphate salts and chromate salts in an amount sufficient to render the polymeric material insoluble in body fluids above 25° C., yet soluble in normal tap water.

It is contemplated that flushable personal hygiene articles, medical, hospital, surgical supplies, disposable household wipes and disposable packaging material may be produced comprising such reversibly insoluble materials.

DETAILED DESCRIPTION OF THE INVENTION

Figure 1:
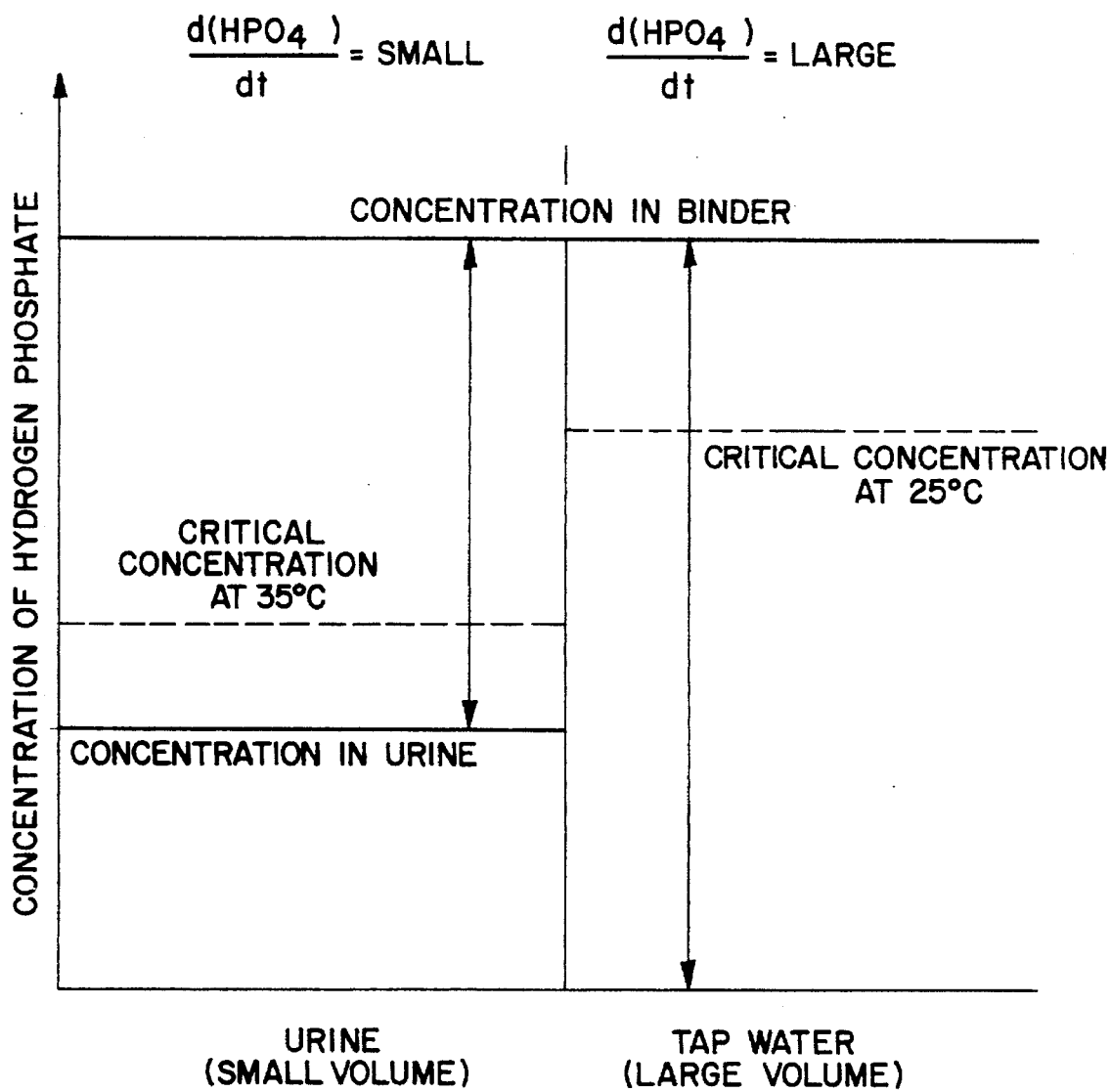
FIG. 1 is a graph illustrating the interrelationship between temperature-dependent solubility, endogenous salt concentration of urine and water, and added salt concentration in a flushable composition for hydroxypropyl cellulose and hydrogen phosphate ion.

Flushable compositions and articles of the present invention have sufficient wet strength for their intended use and are reversibly water insoluble in the presence of body waste fluids, yet soluble in the presence of normal tap water. A benefit of the flushable articles of the present invention is that they are not restricted to articles of small size and they do not contain high levels of borate salts or other additives that may be irritable to the skin when in close proximity to the body.

Flushable articles of the present invention may be made up entirely of flushable components, or composed of a mixture of flushable and non-flushable materials. In the former case, the entire article dissolves, disintegrates or disperses in the presence of normal tap water, while in the latter case the flushable components dissolve, disintegrate or disperse in the presence of normal tap water and the flushable article falls apart into pieces small enough to be flushed without causing obstruction.

Definitions

The term "flushable" as used herein means capable of being flushed in a conventional toilet, and being introduced into a municipal sewage or residential septic system, without causing an obstruction or blockage in the toilet or sewage system. The term "flushable article" as used herein includes, but is not limited to, flushable infant diapers; flushable child care products, such as child training pants; flushable adult care products, such as adult diapers and adult incontinence pads; flushable feminine care products; flushable wipes; flushable medical and surgical care products, such as medical wipes, examination bed coverings, and wound dressings; flushable fabrics; flushable tapes; flushable foams; flushable films; flushable adhesives; flushable elastomeric yarns, flushable household wipes and flushable packaging material.

The term "reversibly water insoluble" as used herein means a substance that is water insoluble in the presence of relatively small volumes of body waste fluids, up to approximately 300 ml, but water soluble in the presence of a relatively large volume of normal tap water, such as the volume of water normally present in a standard toilet bowl. The volume of tap water in many cases may be considered essentially infinite since once a flushable article is introduced into a plumbing system it will be exposed to an endless stream of water. The term "water insoluble" means that the flushable polymers and articles of the present invention comprising the flushable polymers do not dissolve or fragment, and are not soluble or dispersible in the presence of body waste fluids. The term "water soluble" means that the flushable polymers and articles of the present invention comprising the flushable polymers do dissolve or fragment, and are soluble or dispersible in water.

The terms "thermoreversible" or "temperature-sensitive" as used herein means the water solubility of the flushable polymers and articles comprising flushable polymers of the present invention is dependent upon temperature, and optionally on salt concentrations in the flushable polymer formulation. More particularly, the terms "thermoreversible" and "temperature-sensitive" refer to polymers or polymeric compositions that are water soluble at or below 23° C., but which are water insoluble at or above temperatures of 25° C. The terms "thermoreversible" and "temperature-sensitive" also refer to polymers and polymeric compositions that have a storage modulus (G') value of greater than approximately $2 \times 10^5$ dyne/cm$^2$ when in contact with urine at temperatures in the range of 25° C. to 37° C., and a G' value of less than approximately $5 \times 10^3$ dyne/cm$^2$ when in contact with water at temperatures below 23° C.

The term "binder" as used herein encompasses the art accepted usage of the term and means, for example, the material that binds together non-woven polymers or fibers to form a non-woven fabric. A binder may also function as an adhesive. The term "insolubilizing salts" as used herein means salts or additives which, when combined with a polymeric material in the proper amount, forms a temperature-sensitive composition that is reversibly water insoluble in the presence of body waste fluids. "Insolubilizing salts" dissolve or diffuse away from the polymeric material when exposed to normal tap water, rendering the polymeric material water soluble.

Finally, when a salt is combined with a polymer to yield a flushable composition according to the present invention, the term "approximately" as used herein with respect to salt concentration includes concentrations up to twenty percent higher than the stated concentration, or down to twenty percent lower than the stated concentration. The term "approximately" as used herein with respect to temperatures includes temperatures within two degrees of the stated temperature. The term "approximately" as used herein with respect to percent hydrolysis of polymers includes percents hydrolysis within three percents of the stated percent hydrolysis.

Recognizing the difficulties of producing flushable articles due to the above described similarities between body waste fluids, particularly urine, and normal tap water, searches were made and tests were conducted seeking parameters and conditions dissimilar between normal tap water and body waste fluids that could be used to form the basis of flushable articles. Thus, conditions present in body waste fluids that render a polymer insoluble or maintain polymer insolubility, which are not present in normal tap water, were sought. Illustrative of such conditions are hydrogen phosphate ion and urea concentrations, significant levels of which are found only in urine. Another physical parameter that is distinctly different between urine and normal tap water is temperature. Examples of these primary differences between normal tap water and infant urine are illustrated in Table 5.

TABLE 5

| Dissimilarities Between Normal Tap Water And Infant Urine | | |
|---|---|---|
| Parameter | Infant Urine | Tap Water |
| Hydrogen Phosphate Ion | 82–7,361 ppm | 0 ppm |
| Urea | 400–28,6990 ppm | 0 ppm |
| Temperature | >34° C. | <25° C. |

As discussed in the Background of the Invention, no more than 3% of the United States has average surface water temperatures above 29° C. during the months of July and August. However, the temperature of indoor toilet water will be cooler than 29° C. because of the cooler ground water and the air conditioning effect in the house. Additionally, toilet water becomes cooler when it is flushed down into the sewage system and underground piping.

It has been found that the temperature of the diaper liner adjacent to the baby skin during use is between 29° C. and 33° C. Urine at the moment it leaves the body is at body temperature, i.e., 37° C., but subsequently cools down to 30° C.–33° C. at the liner area. The temperature of the outer portion of a diaper or other disposable absorbent article approaches ambient temperature, which for internal spaces generally is approximately 25° C.

This temperature difference between urine and tap water offers an opportunity to design a flushable diaper product by using a temperature-sensitive thermoreversible polymer. One aspect of the present invention is flushable articles containing components that are insoluble at approximately body temperature in the presence of body waste fluids, but which become soluble in cold water. In one embodiment the flushable article is insoluble or non-dispersible above 25° C., or approximately 25° C. in the presence of body waste fluids but soluble or dispersible in water below a temperature of 23° C., or approximately 23° C. In one aspect of the invention, the flushable articles comprise a flushable polymer or composition that has a storage moduli (G') value of greater than approximately $2 \times 10^5$ dyne/cm$^2$ when in contact with urine at temperatures in the range of 25° C. to 37° C., and a G' value of less than approximately $5 \times 10^3$ $dyne/cm^2$ when in contact with water at temperatures below 23° C.

Polymers that exhibit a lower critical solution temperature (LCST) or cloud point close to 25° C. in water are potential suitable materials. Higher cloud point polymers are also suitable if their cloud point can be lowered by the addition of salt(s) or by copolymerization with another component to form a polymeric composition having the desired LCST.

Examples of polymers and their copolymers that exhibit such a behavior include, but are not limited to,
polymethacrylic acid;
polyvinyl pyrrolidone;
polyvinyl methyl ether;
polyvinyl alcohol;
polyethylene oxide;
hydroxy propyl cellulose;
hydroxypropyl methyl cellulose;
methyl cellulose;
ethyl hydroxyethyl cellulose;
isopropyl cellulose;
methyl ether starch;
poly(n-isopropyl acrylamide);
poly(N-vinyl caprolactam);
polyethyl oxazoline;
poly(2-isopropyl-2-oxazoline);
polyvinyl methyl oxazolidone;
polyvinyl methyl oxazolidimone;
poly(2,4-dimethyl-6-triazinylethylene);
and ethylene oxide-propylene oxide copolymers The desired LCST can be achieved by employing copolymerization technology to produce copolymers that exhibit the proper phase transition temperature. Copolymerization permits the selection and commingling of advantageous properties of various polymers. For example, copolymerization is used to control water solubility and wet strength of the flushable polymer. Further, copolymers are produced that have improved thermoplastic properties, which facilitate melt processing.

Such copolymers comprise, for example, a first comonomer that is thermoreversibly insoluble in water, and a second comonomer that is water insoluble irrespective of temperature. Examples of the first comonomers include, but are not limited to polymethacrylic acid, polyvinyl alcohol, polyvinyl pyrrolidone, polyethyl oxazoline, polyethylene oxide, and polyvinyl methyl ether. Examples of the second comonomer include, but are not limited to ethylene, propylene, butylene, alkyl acrylate, alkyl methacrylate, acrylic ester, methacrylic ester, vinyl acetate, styrene, and the like Furthermore, copolymers of ethylene oxide and propylene oxide or butylene oxide are also suitable, as are copolymers of N-n-butyl acrylamide and N-t-butyl acrylamide with acrylamide and N-isopropyl acrylamide.

Other copolymers and combinations of chemical structures will become obvious to one skilled in the art in light of this disclosure, such obvious variations are contemplated to be within the scope of the appended claims.

Additionally, to overcome prior art difficulties associated with (1) making flushable articles by adding salts to solutions in which the articles are suspended, and (2) coating the articles with a high external concentration of salt, it was found that salts or other additives could be incorporated or admixed directly into the bulk of the polymeric material to effectively modulate the reversible water insolubility of the polymeric components and thus form the flushable compositions of the present invention. The added salts are blended or admixed with the polymeric material to form the desired temperature-sensitive reversibly insoluble composition having the salt distributed evenly throughout the bulk of the resulting composition, and not merely associated with the external surfaces of the polymeric material.

Thus, in one embodiment flushable polymers having as an integral component a salt or additive that renders the polymers reversibly insoluble, may be bound by a flushable binder to form a flushable non-woven fabric. In the presence of relatively small volumes of body waste fluids, for example less than approximately 300 ml of urine, the flushable polymers remain insoluble, but upon contact with a relatively large volume of normal tap water, the salt or additive dissolves or diffuses out of the polymer and into the water, rendering the polymer soluble. As a result of contact with water, the flushable article falls apart, permitting the article to be flushed and disposed of in a municipal or private sewage system without obstructing the toilet or sewage system.

Additionally, flushable films, flushable foams, flushable adhesives, and flushable elastomeric yarns can be manufactured by methods well known in the art from flushable polymeric material to which insolubilizing salts have been added. Such films, foams, adhesives and yarns similarly will dissolve in the presence of water as the insolubilizing salt or additive dissolves or diffuses out of the material. In another aspect of the invention, flushable polymers or fibers may be bound together with a non-flushable binder, or alternatively a flushable article may be made by binding together non-flushable materials with a flushable binder or adhesive. In still another aspect of the invention the same flushable polymers or fibers or binders can contain one or more nonflushable ingredients along with the flushable ingredient. In the presence of relatively small volumes of body waste, for example less than approximately 300 ml of urine, the flushable material remains insoluble. However, when the flushable article contacts a relatively large volume of normal tap water, the flushable material dissolves or disintegrates, causing the flushable article to fall apart into small insoluble pieces that are of such a size so as to be flushable themselves.

Yet another aspect of the invention is flushable articles containing components that are insoluble at temperatures of 25° C. to approximately body temperature in the presence of body waste fluids, but which become soluble in cold water. The general relationship between added salt concentration, temperature and polymer solubility are illustrated in FIG. 1, where the ordinate axis reflects a particular salt concentration, in this case hydrogen phosphate ion, and the vertical double arrow lines represent the change in salt concentration under differing conditions. For urine, the endogenous salt concentration is insufficient to ensure polymer insolubility at approximately body temperature. Thus additional salt is incorporated into a flushable binder of which the flushable article is made. This guarantees that the article maintains its structural integrity and wet strength in the presence of body waste fluids while the article is worn. Subsequently, when the article is placed in normal tap water the salt diffuses out of the binder, illustrated by the double arrow vertical line, thus rendering it soluble at normal tap water temperature.

In a desired embodiment the flushable article is insoluble above approximately 25° C. in the presence of body waste fluids but soluble in water below a temperature of approximately 23° C. However, finding a flushable material that meets these criteria is not easily accomplished. For example, one temperature-dependent reversibly water insoluble polymer, Klucel®—a hydroxypropyl cellulose available from Aqualon, Co. of Wilmington, Del., will not precipitate, and, therefore, is soluble in urine as shown in Table 8.

TABLE 8

Effect of Various Urine Salts On The Temperature-Dependent Solubility of Hydroxypropyl Cellulose

| Salt | Critical Salt Concentration For Phase Change at 25° C. (wt %) | Salt Conc. in Urine (wt %) |
| --- | --- | --- |
| Disodium Phosphate | 2 | <0.74 |
| Sodium Sulfate | 5 | <0.35 |
| Sodium Carbonate | 5 | 0 |
| Sodium Chloride | 10 | <1 |
| Calcium Chloride | 50 | <0.018 |

In some cases the critical phase change temperature at which a particular flushable material becomes insoluble may be modulated by the addition of salts to the material. For example, increasing salt concentration decreases the temperature at which hydroxypropyl cellulose precipitates as shown in Table 9.

TABLE 9

Change In Hydroxypropyl Cellulose Precipitation Temperature As A Function Of Salt Concentration

| Concentration (wt %) | Precipitation Temperature (°C.) |
| --- | --- |
| NaCl | |
| 0% | 41° C. |
| 1% | 38° C. |
| 5% | 30° C. |
| 10% | Room Temperature |
| $Na_2HPO_4$ | |
| 0.5% | 36° C. |
| 1.2% | 30° C. |
| 2% | Room Temperature |

For another temperature sensitive reversibly insoluble polymer, polyvinyl alcohol, the degree of hydrolysis of the polymer is critical. Hydrolysis is the process whereby, for example, an acetate side chain on the polymer is hydrolyzed to a hydroxyl group. There is an inverse relationship between the percent hydrolysis and the temperature at which polymer phase change occurs. For example, polyvinyl alcohol having 80.3% hydrolysis has a gel point of 49.7° C., whereas at 71.6% hydrolysis the gel point is 31.7° C.

Accordingly, polyvinyl alcohol polymer-containing compositions of the present invention utilize polyvinyl alcohol polymers having a percent hydrolysis of less than approximately 75%. A desirable flushable composition comprises polyvinyl alcohol that has a degree of hydrolysis of less than 75% and a salt selected from the group consisting of sulfate salts, citrate salts, phosphate salts and chromate salts.

Other desired embodiments include (1) a flushable composition comprising polyethyl oxazoline and a salt selected from the group consisting of phosphate salts, sulfate salts, carbonate salts, and halide salts (2) a flushable composition comprising polyvinyl pyrrolidone copolymer and an inorganic salt, particularly where the salt is ammonium sulfate, and (3) a flushable composition comprising hydroxypropyl cellulose and an inorganic salt, wherein the composition is reversibly water insoluble in the presence of body waste fluids at temperatures above approximately 25° C., but soluble or dispersible in the presence of normal tap water at temperatures below approximately 23° C. More desirable still are embodiments wherein the flushable composition has a storage modulus (G') value of greater than approximately $2 \times 10^5$ dyne/cm$^2$ when in contact with urine at temperatures in the range of 25° C. to 37° C., and a G' value of less than approximately $5 \times 10^3$ dyne/cm$^2$ when in contact with water at temperatures below 23° C.

The flushable article of the present invention made with flushable temperature sensitive polymers may be made entirely of temperature sensitive flushable materials, or may contain flushable as well as non-flushable materials. Additionally, flushable articles may also be made by mixing various different types of flushable materials.

Two different methods for determining wet strength performance in product uses and dispersibility in the toilet bowl have been employed.

Dispersibility

A 'Shake test' was used to evaluate the dispersibility of polymer samples. The polymer solution was treated on a wet-laid fabric (as described in Example 3). A 2"×2" polymer sample was soaked in a 125 ml Erlenmeyer flask containing 100 ml water and placed on a wrist action shaker (Model 75) from Burrell Corporation of Pittsburgh, Pa. The sample was shaken for up to a maximum of 30 minutes at the maximum setting. The condition of sample break-up level in the flask was monitored periodically. After the tests, the sample was examined for the degree of break-up, which was estimated visually. The sample was considered to pass the shake test if the sample was broken into more than 5 pieces or totally dissolved.

Tensile strength

A wet-laid nonwoven web, described in Example 3, was saturated with the flushable binder solution and the treated web was dried at 90° C. The wet tensile strength of the flushable compositions was tested by subjecting samples to a solution containing 0.9% NaCl and 30 ppm calcium chloride for 30 minutes. Wet tensile strength of each sample was measured using a tensile strength measuring device, such as an instrument available from Sintex. Tests were conducted at room temperature only because the instrument was not equipped to measure tensile strength at elevated temperatures.

Moduli

The wet strength of the flushable polymers was also measured by determining the storage moduli of the polymers. The dynamic mechanical response of the polymers as a function of temperature was measured using a Rheometrics Dynamic Spectrometer 2 (RDSII) from Rheometrics, Inc. of Piscataway, N.J. The samples were placed between a pair of serrated parallel plates having a diameter of 25 mm and the plates were separated by a distance of about 2 mm. The storage moduli (G'), loss moduli (G"), and their ratio (G"/G') or tan delta, were recorded. The storage moduli are of interest because G' is related to the rigidity of the polymer at a specific temperature and solution environment.

A majority of the wet strength tests were performed using this method because of the ability to control the temperature during the test. Also, this method provides a direct measurement of the effect of temperature on polymer samples under constant water content and salt content conditions.

It was found that a polymer sample having a G' value of greater than $2 \times 10^5$ dyne/cm$^2$ in contact with an urine environment is able to provide sufficient wet strength as a diaper liner during use. On the other hand, a polymer sample having a G' value of less than $5 \times 10^3$ dyne/cm$^2$ in tap water is considered to be able to be dispersed in toilet bowl.

A series of examples illustrating the present invention are set forth below. Examples 12, 13 and 17–29 are prophetic.

EXAMPLE 1

Polymethacrylic Acid and Copolymers

Concentrated solutions of polymethacrylic acid (PMA) in water form thermoreversible gels. When a concentrated solution of PMA is warmed it coagulates like albumin and, after sufficient time, phase separation occurs—a dilute sol is formed above a concentrated gel. The phase separation is completely reversible.

Also, there is a critical concentration range (CCR) that is dependent on the degree of polymerization (DP) of the polymers. For a DP of 3500, the CCR is about 7% w/w in water. Below the CCR, the solution had no detectable rigidity, but above the CCR the rigidity increased sharply over a concentration range of about 7% to 8% w/w in water. Within the CCR, the rigidity increases with temperature between 30.0° C. and 47.5° C. In contrast to polymethacrylic acid, polyacrylic acid does not exhibit similar thermoreversible gelation behavior despite the fact that they differ only by a methyl group attached to the carboxylic acid group.

The chemical structures of polymethacrylic acid and polyacrylic acid are as follow:

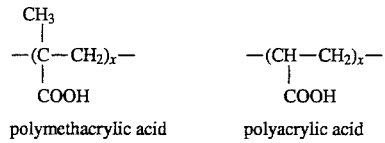

Copolymers of methacrylic acid are of interest because homopolymers of methacrylic acid are highly soluble in water at low concentration and may become unstable in a flushable product during use. By copolymerization a less soluble component can be introduced into the polymer backbone to alter and control its water dissolution rate. Another advantage of copolymers is cost consideration and process flexibility. Copolymers of methacrylic acid are prepared by emulsion polymerization and generally supplied as latex solution. Still another benefit of copolymers is that polymethacrylic acid has been reported to irritate human skin and eyes such that it will prevent its use in many products that come in contact with skin. Copolymers reduce or eliminate the irritating effect that occurs when polymethacrylic acid comes in contact with the skin.

Copolymers of methacrylic acid can not be easily differentiated from acrylic acid based polymers without chemical analysis due to proprietary nature of many commercial products. Therefore, commercially available polymers containing carboxylic acid group were evaluated for their temperature response in moduli. Three commercial polymers containing carboxylic acid group, Acrysol ASE-95, Rhoplex HA-8 and Rhoplex NW-1715 supplied by Rohm & Haas Co. of Philadelphia, Pa. were used for comparison purposes. The first polymer exhibits excellent temperature response while the other two compositions were found to be not meeting the criteria required for use in a flushable composition, as discussed more fully below.

EXAMPLE 2

Polymethacrylic acid (PMA) having molecular weight of about 100,000 was obtained from Polysciences, Inc. of Warrington, Pa.

A polymer gel was prepared by mixing 18% w/w PMA with water. The wet storage moduli as a function of temperature is given as follow:

TABLE 11

| Temperature, °C. | Storage modulus, dyne/sq. cm. |
| --- | --- |
| 18.1 | $1.345 \times 10^3$ |
| 18.6 | $2.207 \times 10^3$ |
| 19.6 | $6.228 \times 10^3$ |
| 21.1 | $7.082 \times 10^4$ |
| 22.8 | $5.482 \times 10^5$ |
| 24.6 | $1.952 \times 10^6$ |
| 26.6 | $4.395 \times 10^6$ |
| 28.7 | $7.741 \times 10^6$ |
| 31.0 | $1.166 \times 10^7$ |
| 33.2 | $1.646 \times 10^7$ |
| 35.5 | $2.136 \times 10^7$ |
| 37.8 | $2.468 \times 10^7$ |

Figure 2:
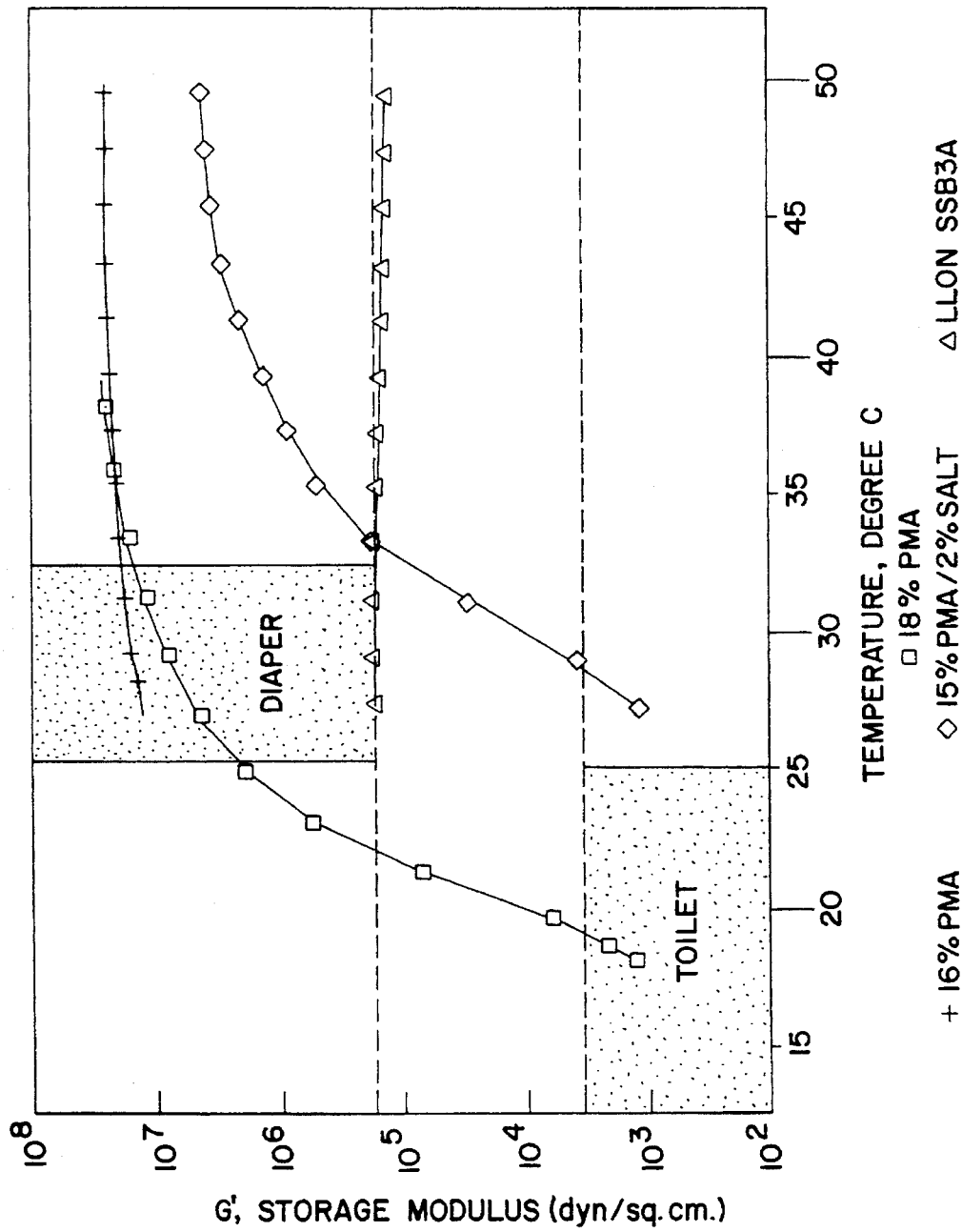
FIG. 2 is a graph of storage moduli (G') values as a function of temperature for various polymethacrylic acid polymer preparations.

The 'wet' polymer becomes stronger at elevated temperatures. See FIG. 2 for a plot of G' values as a function of temperature for PMA having various degree of hydration.

EXAMPLE 3

Acrysol ASE-95, a copolymer that containing carboxylic acid groups, was examined as for its utility as a flushable material component. Acrysol ASE-95 is generally used as a thickener and rheology modifier in the paper industry. It is an emulsion copolymer containing carboxylic acid groups and has an effective equivalent weight of solid (weight of polymer solids exactly neutralized by 40 grams of NaOH) of 124.

A wet-laid nonwoven web based on a blend of 60% 1.5 denier ¼" PET staple fibers and 40% Abaca pulp was saturated with the ASE-95 solution and the treated web was dried at 90° C. 0.125% Parez NC 631, is a wet strength chemical, was added to the web for easily handling during the wet laid process. This chemical does not contribute any wet tensile strength in water or urine. The add-on level was 20%. The wet tensile strength for a 3" wide sample in 0.9% NaCl/30 ppm CaCl$_2$ solution was measured to be 2.83 lbs. at room temperature. The sample passed the shake test.

EXAMPLE 4

A binder solution was prepared by combining 70% of Acrysol ASE-95 and 30% of Emulsion E-1847. Emulsion E-1847 is a formaldehyde free acrylic binder and is supplied as a 44% solution from Rohm and Haas Co. The binder solution was treated on the wet-laid fabric as described in Example 3 above. The add-on level was 23%. The wet tensile strength for a 3" wide sample in 0.9% NaCl/30 ppm $CaCl_2$ solution was measured to be 3.66 lbs. at room temperature. The sample passed the shake test.

The treated fabric was subjected to an aging test at 130° F. for 24 hrs. The wet tensile strength increased to 9.13 lbs. The sample failed the shake test if the sample was freshly soaked, but passed the shake test if the sample was pre-soaked for 24 hr.

For comparison purposes, another sample of the wet-laid web made from the same lot was treated with Rhoplex HA-8 latex solution supplied by Rohm & Haas Company of Philadelphia, Pa. HA-8 is a water insoluble acrylic polymer. The add-on level was 15.9%. The wet strength for a 3" wide sample in 0.9% NaCl/30 ppm $CaCl_2$ solution was measured to be 6.35 lbs. The treated fabric was aged at room temperature for more than a week. The wet tensile strength increased to 7.03 lbs. As expected, both the fresh and aged samples remained intact (i.e. failed) in the shake test.

EXAMPLE 5

A semi-rigid polymer gel was prepared by mixing 19% of ASE-95 with water. The wet storage moduli as a function of temperature were measured, the results of which are shown in Table 12.

TABLE 12

| Temperature, °C. | Storage modulus, dyne/sq. cm. |
| --- | --- |
| 19.7 | $2.545 \times 10^3$ |
| 20.3 | $3.902 \times 10^3$ |
| 21.3 | $5.951 \times 10^3$ |
| 22.5 | $1.088 \times 10^4$ |
| 23.8 | $2.055 \times 10^4$ |
| 25.3 | $3.311 \times 10^4$ |
| 26.8 | $5.384 \times 10^4$ |
| 28.4 | $7.598 \times 10^4$ |
| 30.0 | $6.822 \times 10^4$ |
| 31.6 | $8.294 \times 10^4$ |
| 33.4 | $1.520 \times 10^5$ |
| 35.2 | $2.681 \times 10^5$ |

Figure 3:
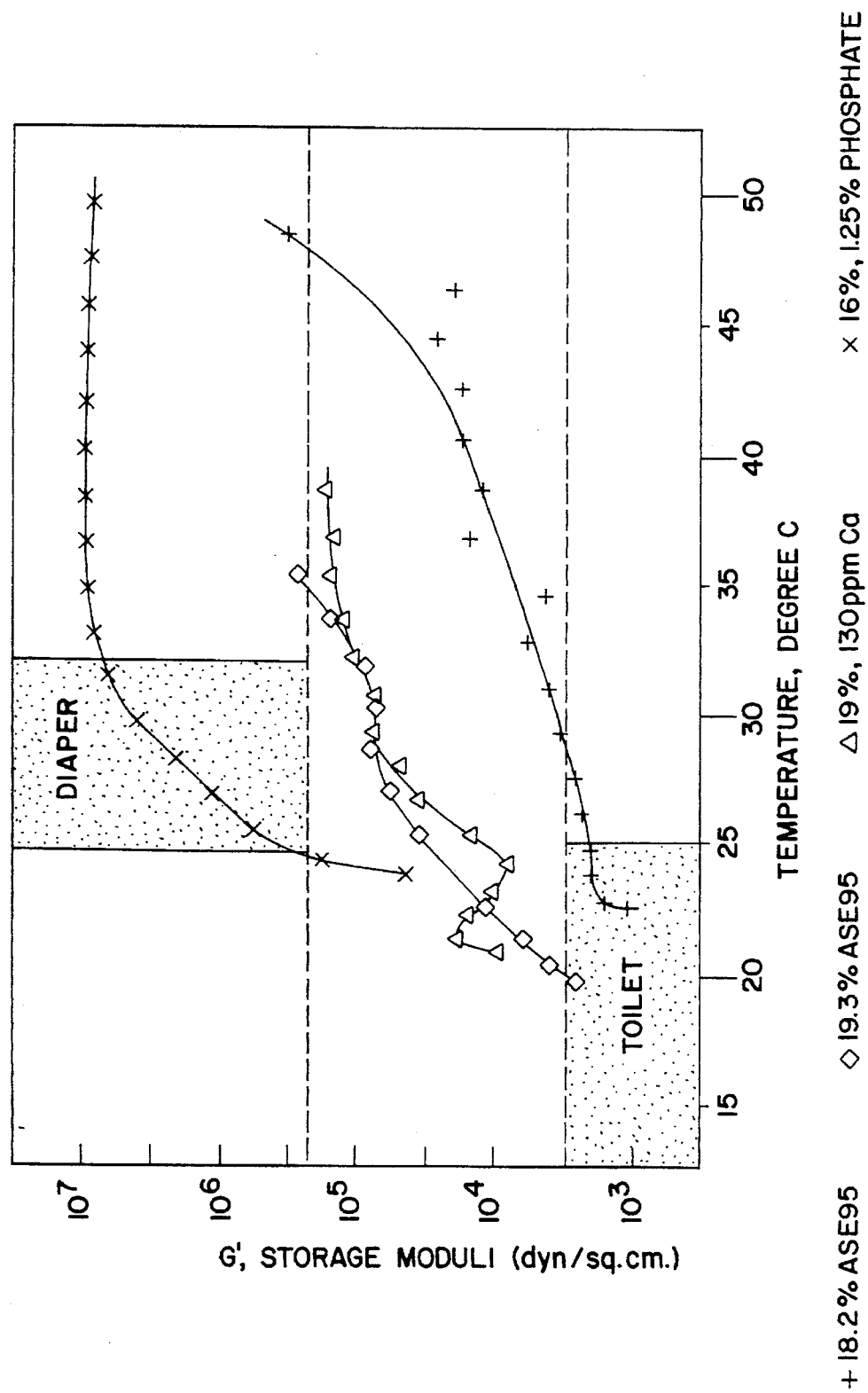
FIG. 3 is a graph of storage moduli (G') values as a function of temperature for various Acrysol ASE95 polymers preparations.

FIG. 3 is a plot of G' values as a function of temperature for Acrysol ASE-95 and ASE-95 having 1.25% sodium phosphate or 130 ppm $Ca^{2+}$. The rigidity of ASE-95 is enhanced with the presence of sodium phosphate or calcium chloride. At 130 ppm $Ca^{2+}$, which is equivalent to the maximum hardness found in most tap water, the storage modulus G' at room temperature is low. Indicating that ASE-95 is dispersible in tap water and therefore is flushable.

For comparison purposes, two different water insoluble polymers, Rhoplex HA-8 and Rhoplex NW-1715, obtaining from Rohm and Haas Company were studied. Rhoplex HA-8 is a nonionic self-crosslinking acrylic polymer. It was supplied as 45.5% latex solution. It has a glass transition temperature of −10° C. Rhoplex NW-1715 is a formaldehyde-free acrylic nonwoven binder. It has a glass transition temperature of −15° C. and it was supplied as 44% latex solution.

Dry polymer samples were obtained by evaporating the solvent from latex solutions. After 3 days, the dry samples were resoaked in distilled water overnight. The 'wet' solids were immediately removed from the solution and placed between two serrated plates of a rheometric dynamic spectrometer and the storage moduli were obtained.

TABLE 13

| Temperature, °C. | HA-8 dyne/sq. cm. | NW-1715 dyne/sq. cm. |
| --- | --- | --- |
| 25.8 |  | $2.812 \times 10^5$ |
| 28.7 | $2.256 \times 10^5$ |  |
| 39.8 |  | $2.687 \times 10^5$ |
| 42.1 | $2.023 \times 10^5$ |  |

It is clear that the storage modulus for both acrylic polymers decreases as the temperature increases. There is no advantage of these polymers in terms of temperature-dependent solubility or dispersibility. However, these polymers have been used as a binder for a wet-laid fabric. The treated fabrics showed sufficient wet strength in diaper liner during use.

The HA-8 treated wet-laid web was found to have sufficient strength as diaper liner during use. Accordingly, HA-8 was used as a control and its wet strength performance was used as the target value for the performance requirement of the flushable polymers and compositions of the present inventions for use as a flushable diaper liner.

EXAMPLE 6

Polyvinyl Alcohol

Certain polyvinyl alcohol polymers are suitable for use as flushable material. However, the degree of hydrolysis of the polymer is critical. Hydrolysis is the process whereby, for example, an acetate side chain on the polymer is hydrolyzed to a hydroxyl group. The solubility in water depends on the degree of polymerization and hydrolysis. Fully hydrolyzed (98–99 mol %) poly(vinyl alcohol) (PVOH) is soluble only in hot to boiling water, whereas PVOH becomes more soluble at low temperatures for lower hydrolysis (87–89 mol %) samples. For samples that are less than 80% hydrolyzed, there is an inverse relationship between the percent hydrolysis and the temperature at which polymer phase change occurs.

The chemical structure of polyvinyl alcohol is as follows:

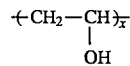

EXAMPLE 7

Polyvinyl alcohol having a hydrolysis of less than 80%, under the trademark of Gohsenol, were obtained from Nippon Synthetic Chemical Industry Co., Ltd. (or commonly refer to Nippon Gohsei) of Osaka, Japan.

The following table lists the polymer samples used in the present invention.

TABLE 14

| Grade name | DH, % | DP | Cloud point, °C. | Polymer concentration, % |
| --- | --- | --- | --- | --- |
| LL-02 | 45–51 | 1045 | * | 30 |
| KZ-06 | 71.6 | 1015 | 32 | 20 & 35 |
| NK-05 | 72–75 | 500 | 39 | 31 |
| KH-17 | 78.5–81.5 | 1040 | 50 | 19 |

DH: degree of hydrolysis

TABLE 14-continued

| Grade name | DH, % | DP | Cloud point, °C. | Polymer concentration, % |
|---|---|---|---|---|

DP: degree of polymerization
(*): water insoluble

Figure 4:
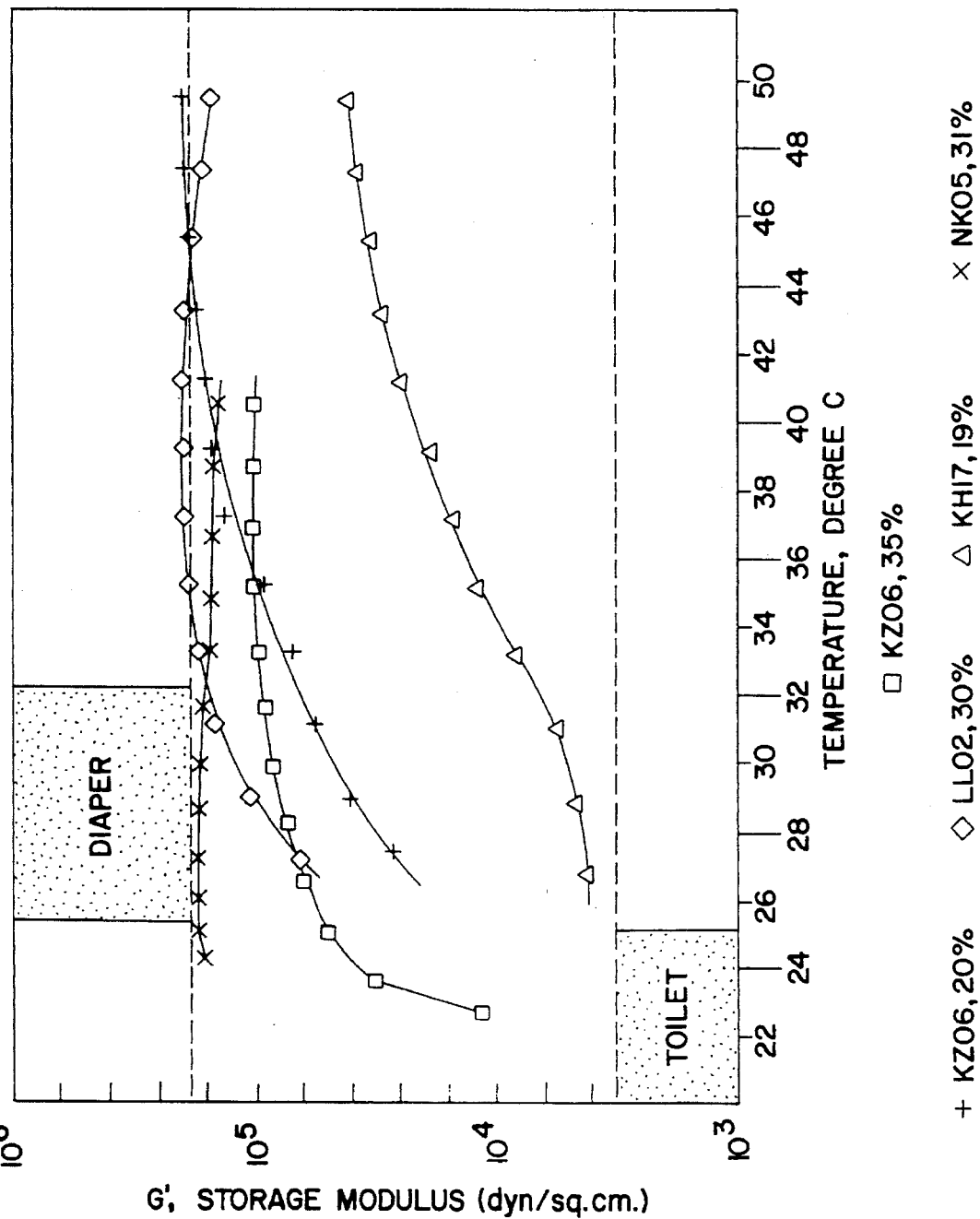
FIG. 4 is a graph of storage moduli (G') values as a function of temperature for various polyvinyl alcohol polymer preparations.

FIG. 4 shows a plot of G' values as a function of temperature for different grades of polyvinyl alcohol. The polymer concentration is shown in the last column of Table 14, above. LL-02 grade shows excellent temperature-dependent phase change in the desired temperature range between the temperature of tap water (20° C.) and the temperature of body waste fluids (34° C.). Although LL-02 is water-insoluble, it forms a soft hydrogel in water at low temperature and it is dispersible in a tap water environment (the G' value drops below $5 \times 10^3$ dyne/cm$^2$ as the polymer concentration decreases to less than 30%). Both KZ-06 and KH-17 show a drastic increase in G' value as the solution temperature approaches the cloud point of the polymer. NK-05 grade did not show any temperature-dependent effect.

Figure 5:
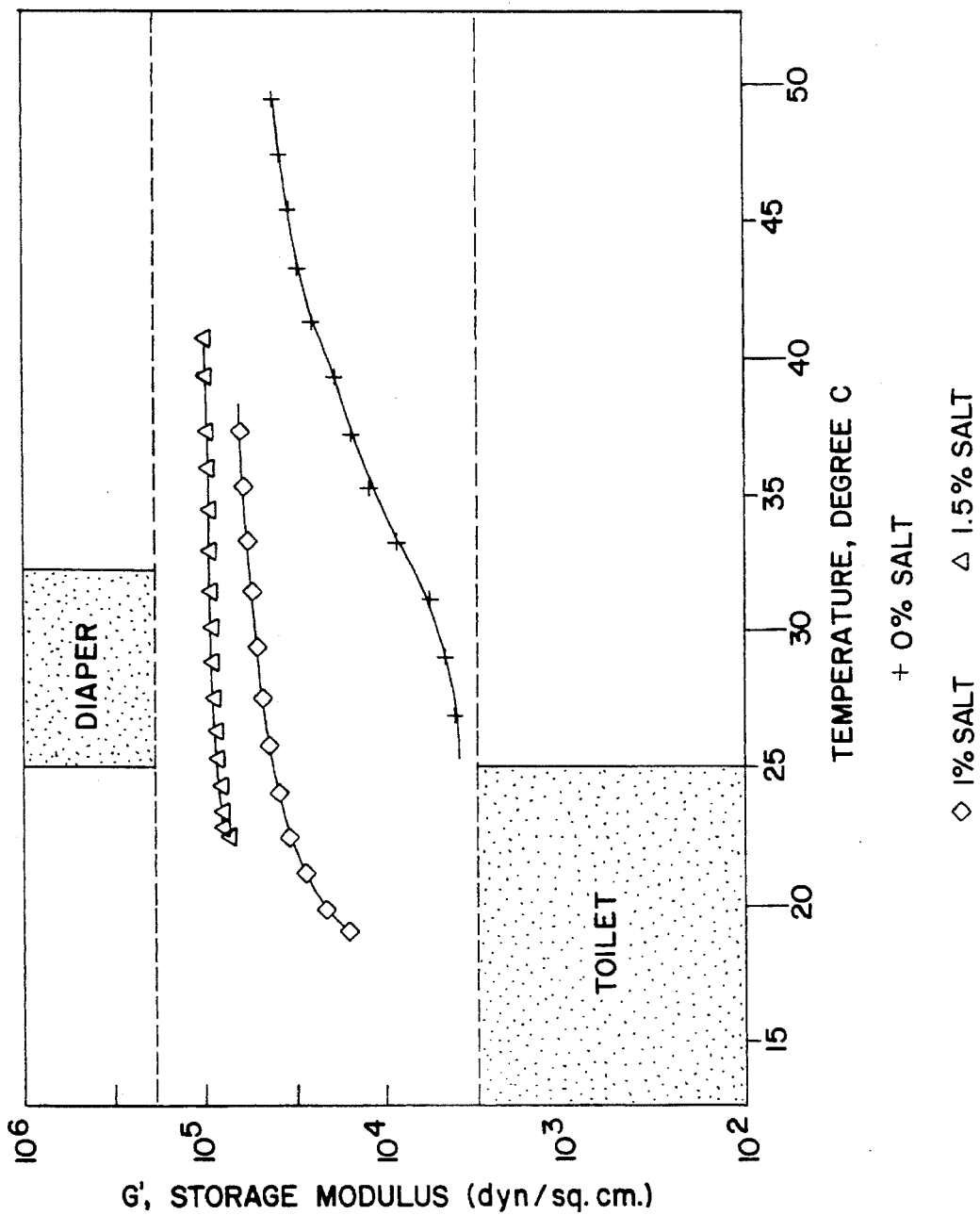
FIG. 5 is a graph of storage moduli (G') values as a function of temperature for various polyvinyl alcohol KH-17 polymer preparations.

FIG. 5 shows the effect of sodium phosphate on G' values for sample KH-17. The presence of salt enhances the rigidity of the polymer. Table 15 shows the polymer concentration and Na$_3$PO$_4$ concentrations of the polyvinyl alcohol KH-17 samples that were measured to yield the results shown in FIG. 5.

TABLE 15

| Polymer Concentration % | Na$_3$PO$_4$ Concentration % |
|---|---|
| 19 | 0 |
| 18.5 | 0.99 |
| 15.5 | 1.94 |

The polyvinyl alcohol grades used in the present invention differ from those used by the prior art (see for example U.S. Pat. Nos. 3,645,928 and 3,692,725). The PVOH used by the prior art are those having high degree of hydrolysis (>87 mol %). The wet strength of these PVOH decreases and become more water soluble with increasing temperature.

EXAMPLE 8

Polyethyl Oxazoline

Polyethyl oxazoline is soluble in water and has a cloud point of between 61° C. and 64° C. depending on molecular weight (See for example, "Solubility and miscibility of polyethyl oxazoline," by P. Lin, C. Clash, E. M. Pearce and T. K. Kwei and M. A. Aponte, Journal of Polymer Science, Part B: Polymer Physics, Vol. 26, pg. 603–619 (1988). The chemical structure is as follow:

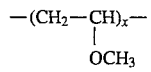

Figure 6:
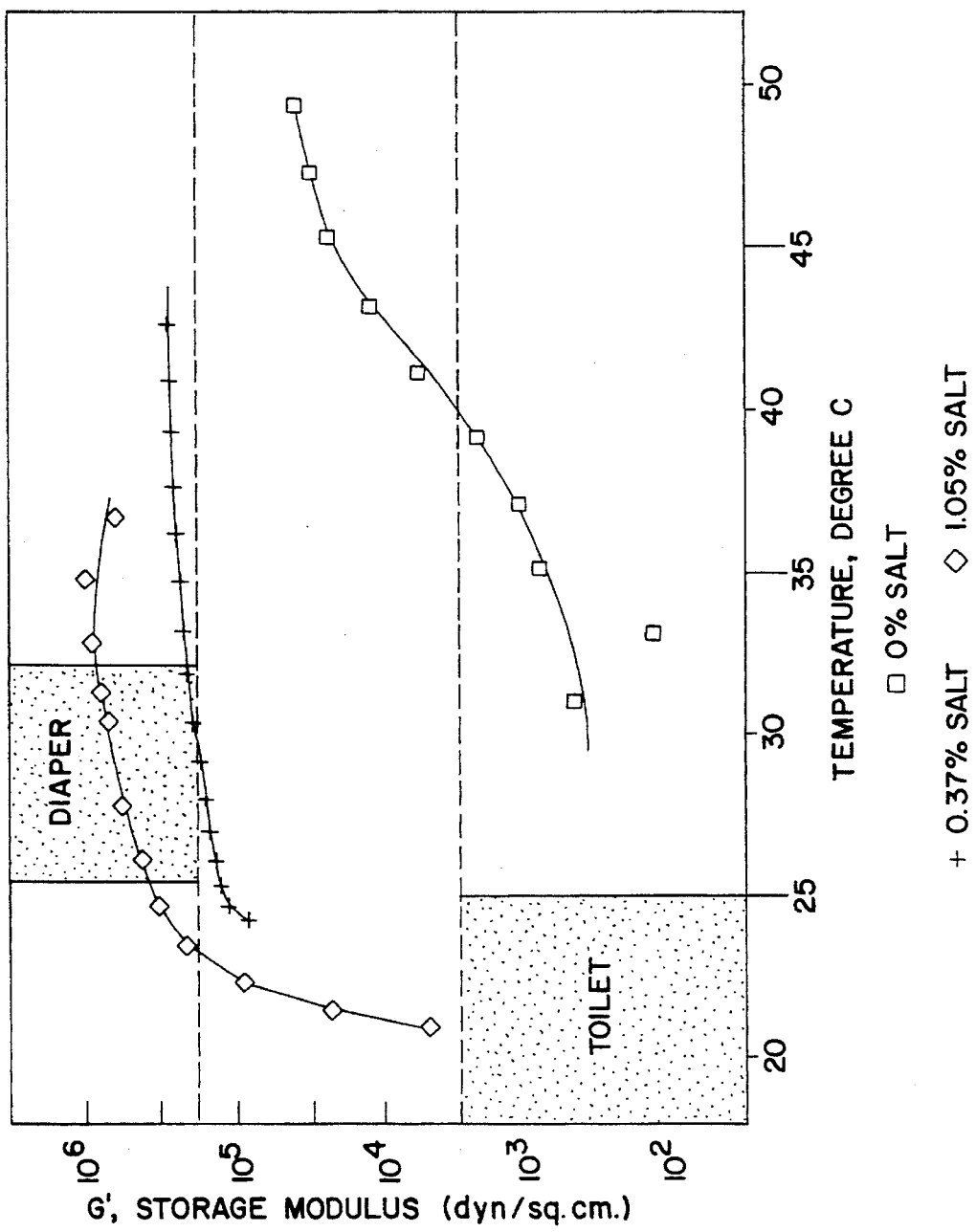
FIG. 6 is a graph of storage moduli (G') values as a function of temperature for various polyethyl oxazoline polymer preparations.

Polyethyl oxazoline having a molecular weight of 500,000 was obtained from Polysciences, Inc. of Warrington, Pa. FIG. 6 shows a plot of G' values as a function of temperature for polyethyl oxazoline having varying amount of sodium phosphate. There are strong temperature- and salt-dependent effects on the storage moduli. Table 16 shows the polymer concentrations and Na$_3$PO$_4$ concentrations of the polyethyl oxazoline samples that were measured to yield the results shown in FIG. 6.

TABLE 16

| Polymer Concentration % | Na$_3$PO$_4$ Concentration % |
|---|---|
| 24.3 | 0 |
| 23.5 | 0.37 |
| 23.4 | 1.05 |

EXAMPLE 9

Polyvinyl Methyl Ether

Polyvinyl methyl ether (PVME or polymethoxy ethylene) is soluble in water in all proportions at room temperature because of hydrogen bonding of water to the polymer ether linkage. Heating aqueous PVME solutions destroys the ether linkage hydration and decreases water solubility. Thus, PVME polymer comes out of water solution at a specific temperature, which is generally known as the cloud point, of 33° C. See, for example, "Vinyl ether monomers and polymers," by E. V. Hort and R. C. Gasman, in Encyclopedia of Chemical Technology, Volume 23, pg. 937–960, 3rd. Edition, published by John Wiley & Sons, New York, N.Y. PVME is widely used as an adhesive. The chemical structure of polyvinyl methyl ether is as follows:

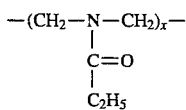

Figure 7:
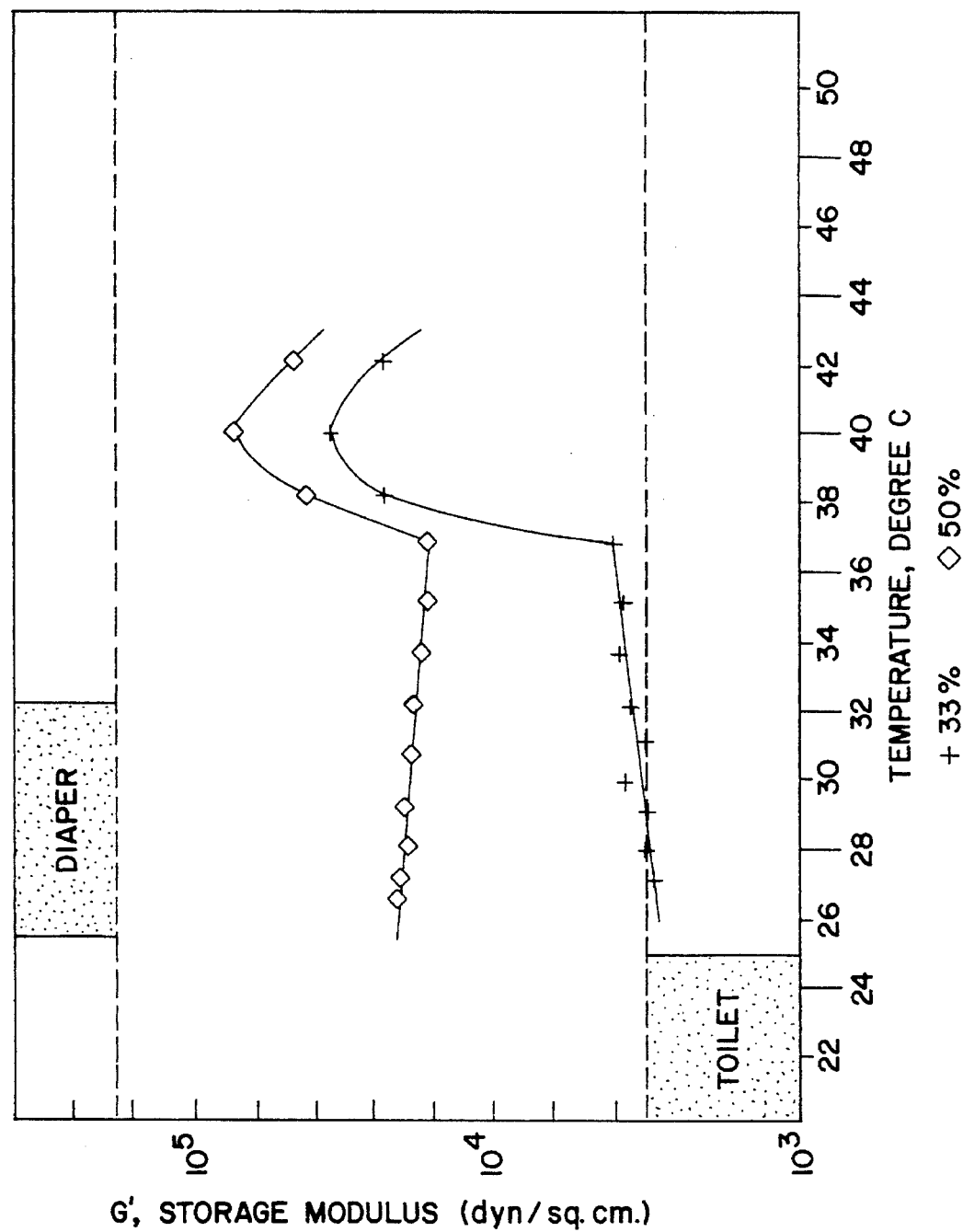
FIG. 7 is a graph of storage moduli (G') values as a function of temperature for various polyvinyl methyl ether polymer preparations.
Figure 8:
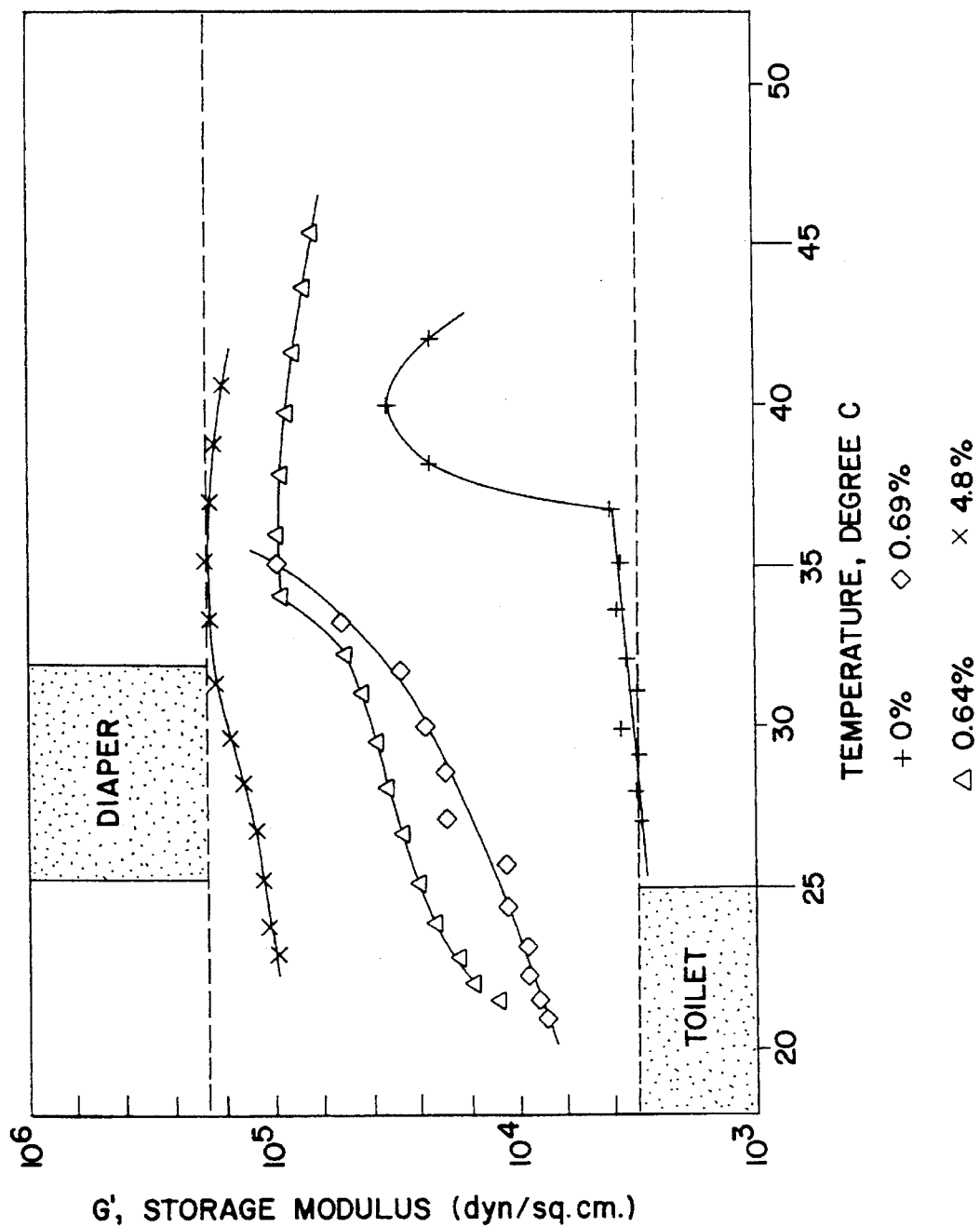
FIG. 8 is a graph of storage moduli (G') values as a function of temperature for various polyvinyl methyl ether polymer preparations containing sodium phosphate.

PVME was obtained from Polysciences, Inc. of Warrington, Pa. as a 50% aqueous solution. FIG. 7 show a plot of G' values as a function of temperature for PVME of various degrees of hydration. Temperature has no effect on the G' value below 37° C., but there is a drastic rise in the G' value around 37° C. FIG. 8 shows a plot of G' values as a function of temperature for PVME having varying amount of sodium phosphate. The presence of salt causes PVME to precipitate out of solution and increases the rigidity of PVME in wet form. Table 17 shows the polymer concentrations and Na$_3$PO$_4$ concentrations of the polyvinyl methyl ether samples that were measured to yield the results shown in FIG. 8.

TABLE 17

| Polymer Concentration % | Na$_3$PO$_4$ Concentration % |
|---|---|
| 33 | 0 |
| 29.4 | 0.69 |
| 29.4 | 0.64 |
| 11.4 | 4.8 |

EXAMPLE 10

Polyvinyl Pyrrolidone Copolymers

Poly(N-vinyl-2-pyrrolidone) (PVP) homopolymer has a theoretical cloud point of 150° C. (See, for example, "Water solubility and sensitivity—hydration effects" by F. Franks, in Chemistry and Technology of Water-soluble Polymers, Ed. by C. A. Finch, Plenum Press, New York, (1983), pg. 157–178. The strong interaction between PVP and inorganic salts, such as ammonium sulfate, has been reported. PVP can be precipitated out of aqueous solution by adding 0.86 molar ammonium sulfate (See for example, "Effect of Electrolytes on solution behavior of water soluble macromolecules," by M. J. Garvey and I. D. Robb, Journal of the Chemical Society, Faraday Trans. I, volume 75, pg. 993–1000 (1979)).

It is thus of interest to investigate copolymers of PVP with a less soluble comonomer, such as vinyl acetate. A number of PVP/VA copolymers are used as hairspray resins, tablet excipients, and adhesives. For example, a PVP/VA copolymer is commercially available from International Specialty Products (formerly GAF Chemicals Co.) of Charlotte, N.C. The chemical structure of PVP/VA copolymers is as follows:

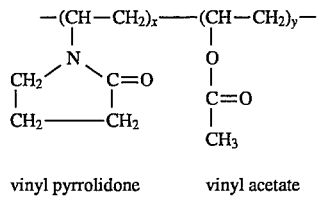

vinyl pyrrolidone     vinyl acetate

Copolymers E335 and E535 were obtained from ISP as 48–52% polymer solution (anhydrous ethanol as solvent). E335 has 30 mole % of PVP and 70 mole % vinyl acetate. E535 has 50 mole % of PVP and 50 mole % of vinyl acetate. Dry polymer samples of both E335 and E535 were obtained by evaporating the solvent. The dry polymer samples were then mixed with water to different degrees of hydration for wet modulus measurement. E335 is slightly soluble in water and the solubility increases with increasing PVP content.

Figure 9:
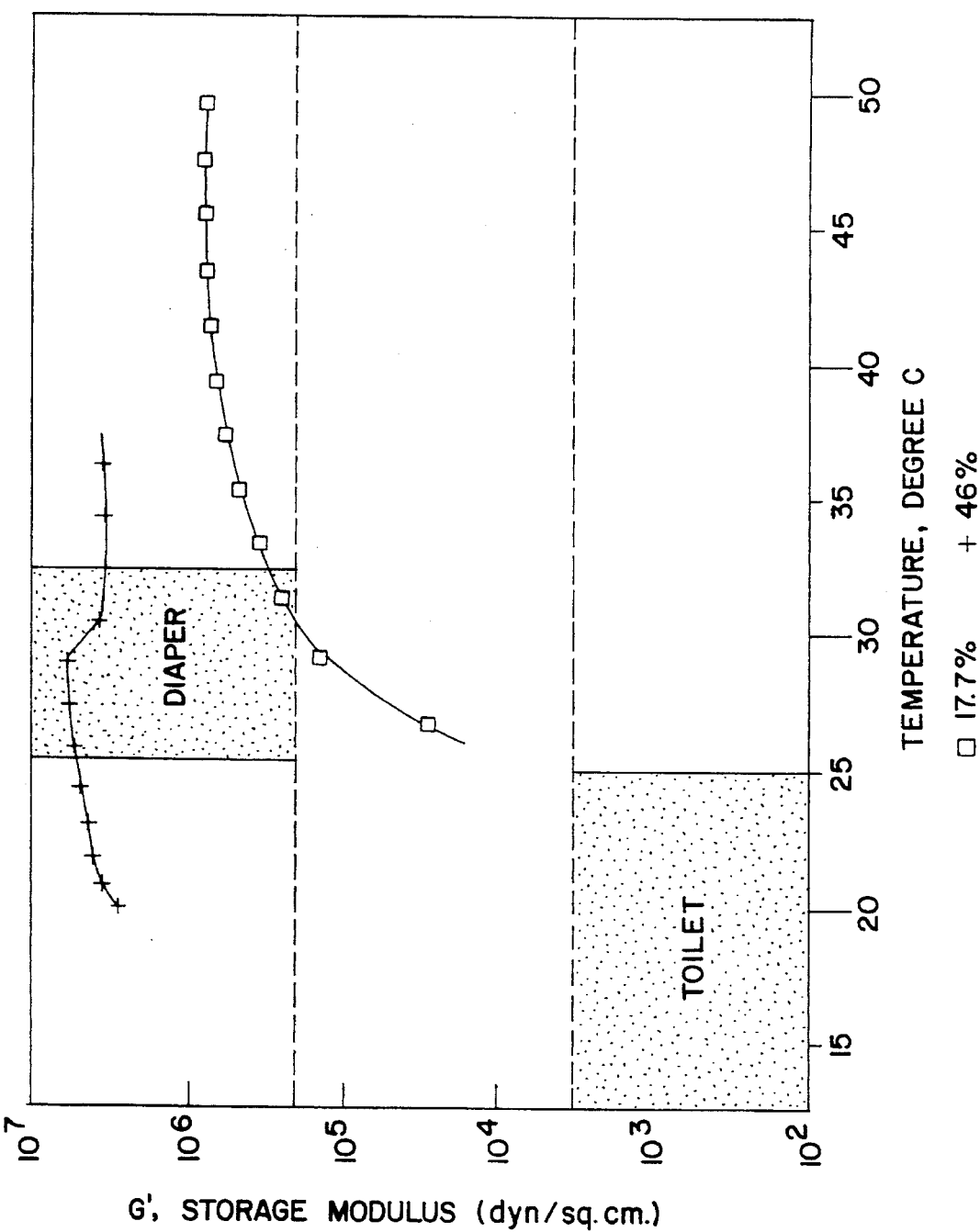
FIG. 9 is a graph of storage moduli (G') values as a function of temperature for various polyvinyl pyrrolidone/vinyl acetate E335 polymer preparations.
Figure 10:
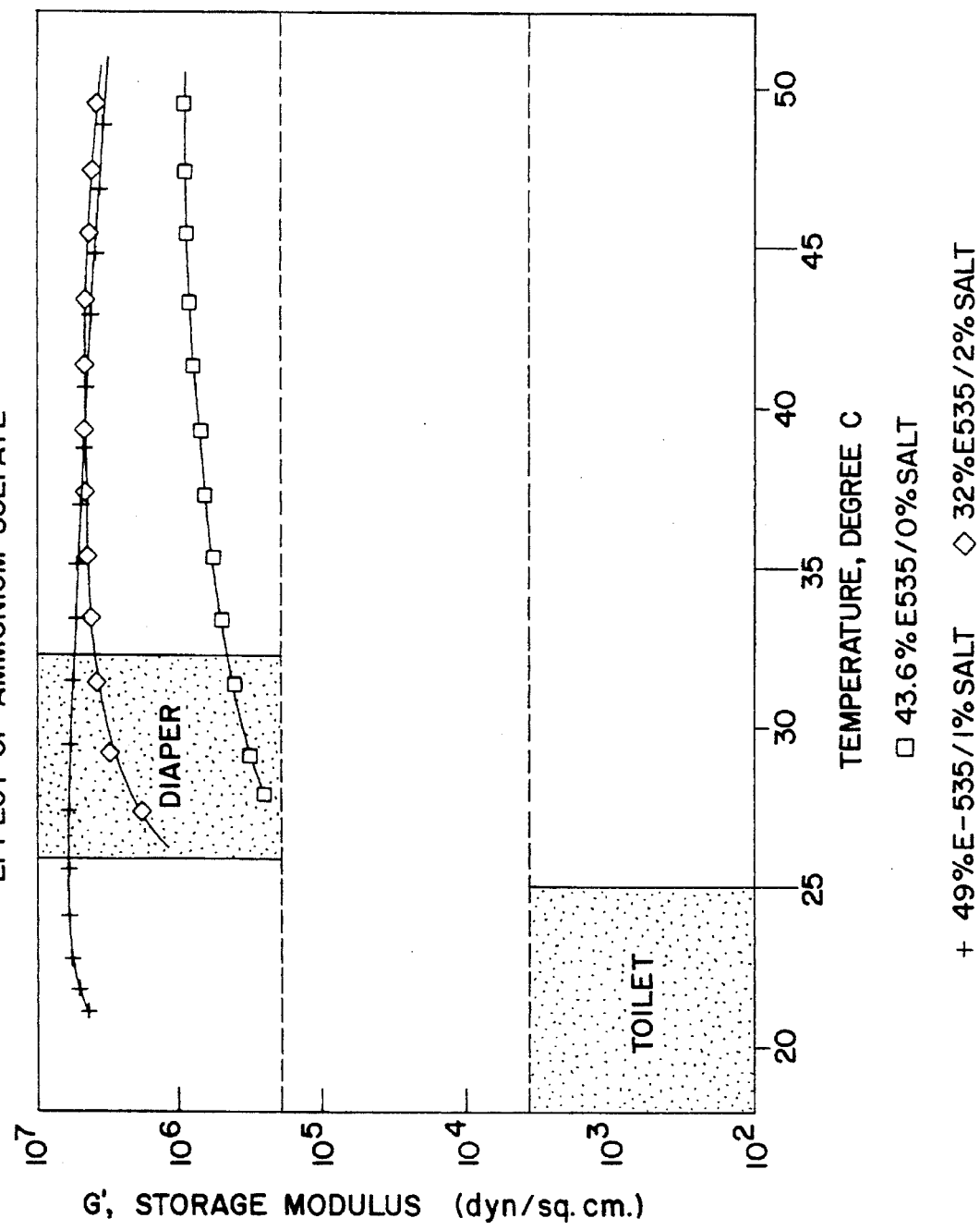
FIG. 10 is a graph of storage moduli (G') values as a function of temperature for various polyvinyl pyrrolidone/vinyl acetate E535 polymer preparations.

FIG. 9 shows a plot of G' values as a function of temperature for E335 of different degrees of hydration. The temperature-dependent effect is stronger for more hydrated samples. FIG. 10 shows a plot of G' values as a function of temperature for E535 in combination with ammonium sulfate.

EXAMPLE 11

Hydroxypropyl Cellulose

Hydroxypropyl cellulose (HPC) has a cloud point of 43° C. (See for example, "Phase diagrams of nonionic polymer-water systems," by G. Karlstrom, A. Carlsson and B. Lindman, J. Phys. Chem., Vol. 94, pg. 5005–5015 (1990)). HPC is commercially available from Aqualon Co. of Wilmington, Del. under the trademark of Klucel. The chemical structure of HPC is as follows:

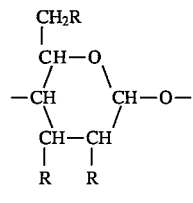

where R = OCH$_2$CHCH$_3$
               |
               OH

Figure 11:
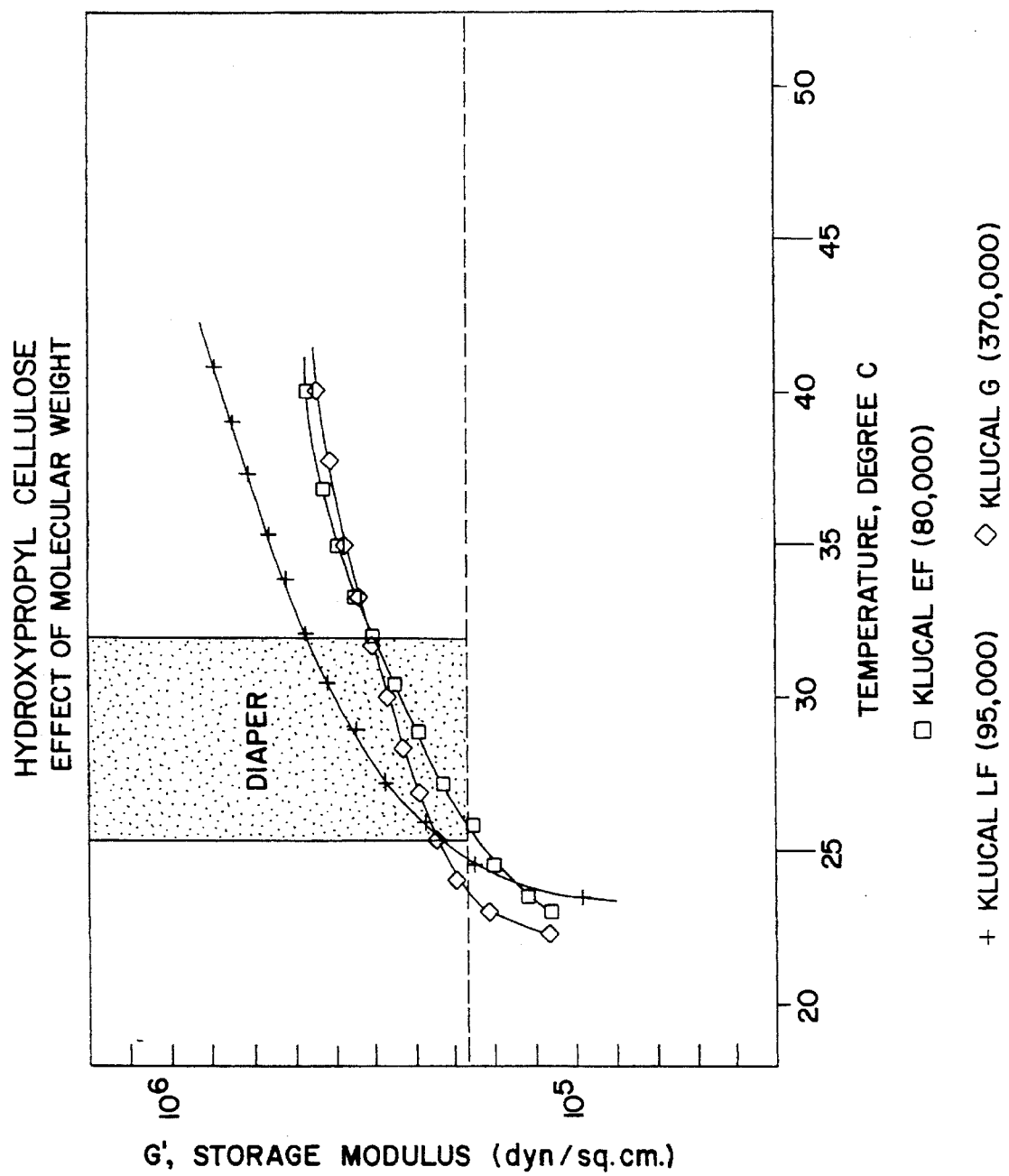
FIG. 11 is a graph of storage moduli (G') values as a function of temperature for various hydroxypropyl cellulose polymer preparations.

FIG. 11 shows a plot of G' values as a function of temperature for Klucel having different molecular weight (MW). The MW for Klucel EF, Klucel LF and Klucel G is 80,000, 95,000, 370,000, respectively. There is a small effect of MW on G' value.

Figure 12:
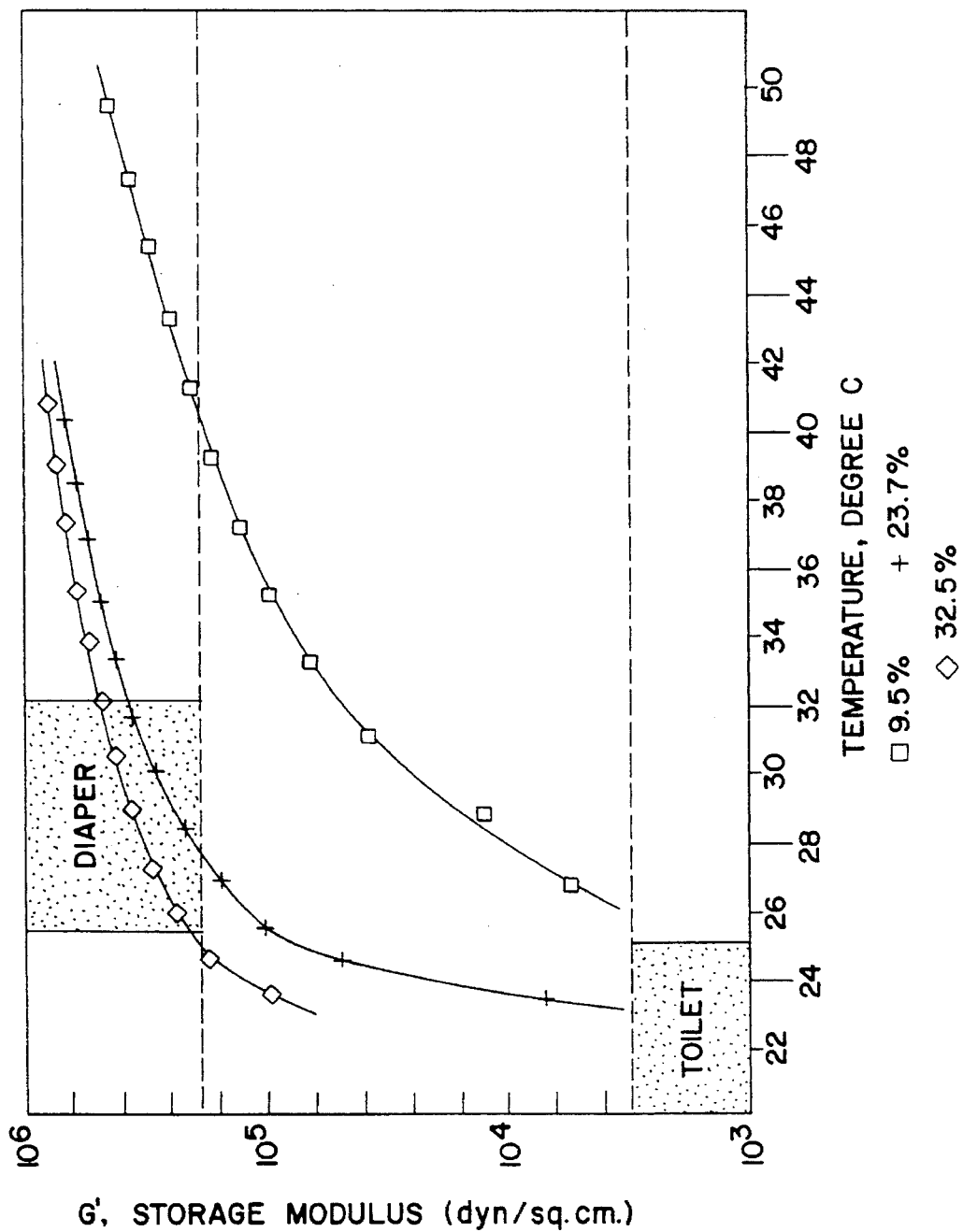
FIG. 12 is a graph of storage moduli (G') values as a function of temperature for various hydroxypropyl cellulose polymer preparations containing various additives.
Figure 13:
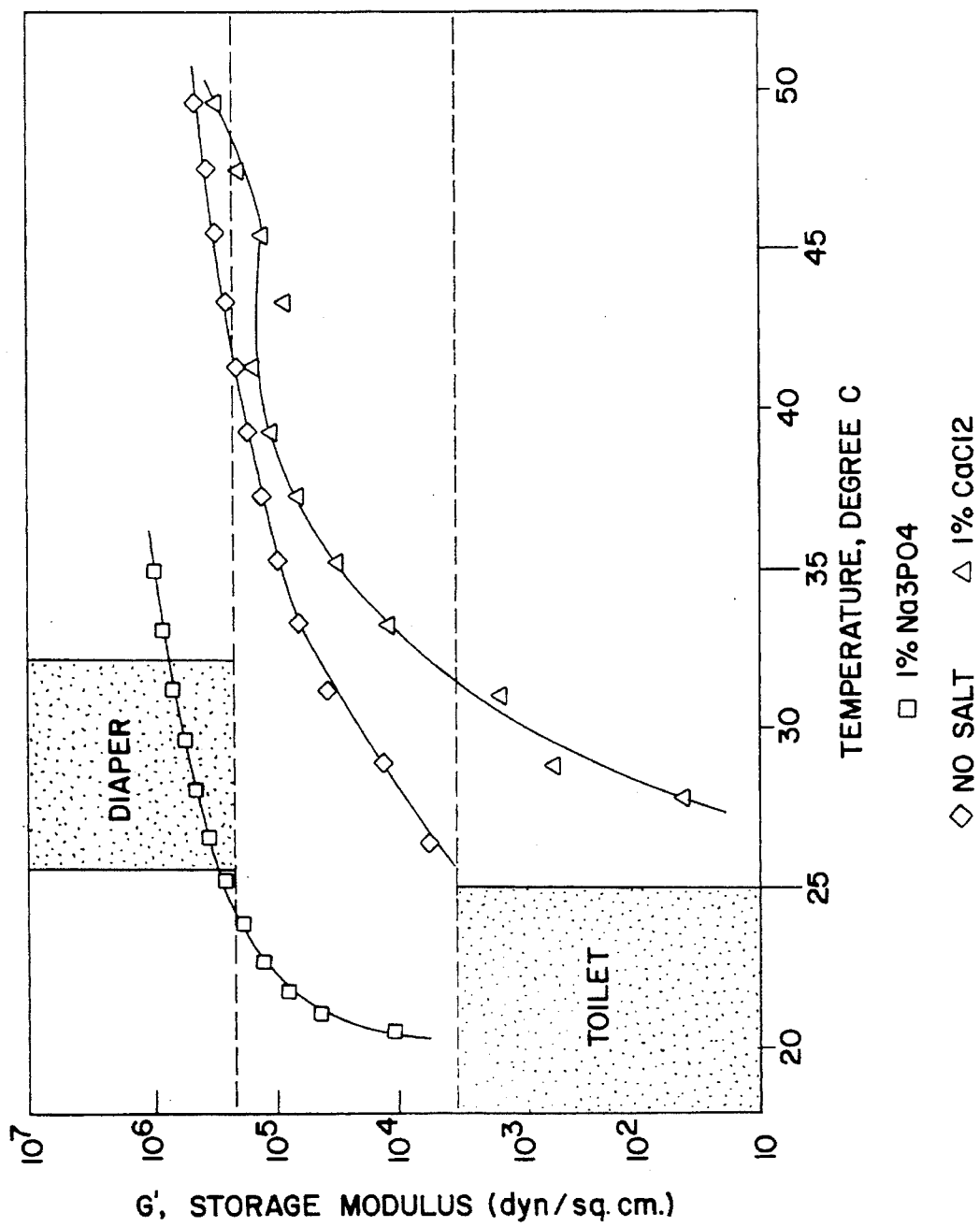
FIG. 13 is a graph of storage moduli (G') values as a function of temperature for various hydroxypropyl cellulose polymer preparations containing various salts.

FIG. 12 shows a plot of G' values as a function of temperature for Klucel LF of various degree of concentration. FIG. 13 shows the effect of sodium phosphate on G' values for Klucel LF. The presence of salt causes Klucel to precipitate out of solution and this increases the wet rigidity of the polymer. Table 18 shows the polymer concentrations and Na$_3$PO$_4$ concentrations of the Klucel LF samples that were measured to yield the results shown in FIG. 13.

TABLE 18

| Polymer Concentration % | Salt % |
|---|---|
| 9.52 | 0 |
| 9.93 | 0 |
| 9.67 | 1.0% Na$_3$PO$_4$ |
| 9.74 | 0.88% CaCl$_2$ |

EXAMPLE 12

Klucel, available from Aqualon Co., whose chemical designation is cellulose 2-hydroxypropyl ether, is combined with 5% by weight NaCl. The polymer and salt may be mixed in an aqueous solution used to saturate a non-woven fabric, which subsequently is dried to remove the water. Alternatively, the polymer and salt may be mixed and heated to form a water-free composition that can be spun or extruded to form the flushable materials such as fibers, films and foams. This flushable material undergoes phase change at approximately 25° C.

EXAMPLE 13

Klucel, available from Aqualon, whose chemical designation is cellulose 2-hydroxypropyl ether, is combined with 1.2% by weight Na$_2$HPO$_4$. The polymer and salt may be mixed in an aqueous solution used to saturate a non-woven fabric, which subsequently is dried to remove the water. Alternatively, the polymer and salt may be mixed and heated to form a water-free composition that can be spun or extruded to form the flushable materials such as fibers, films and foams. This flushable material undergoes phase change at approximately 25° C.

EXAMPLE 14

Methyl Cellulose

Methyl cellulose (MC) has a cloud point of 49° C. (See for example, "Studies on sol-gel transformations. I The inverse sol-gel transformation of methyl cellulose in water," by E. Heymann, Transactions of the Faraday Society, vol. 31, pg. 846–864 (1935) and "Phase diagrams of nonionic polymer-water systems," by G. Karlstrom, A. Carlsson and B. Lindman, J. Phys. Chem., Vol. 94, pg. 5005–5015 (1990)). Methyl cellulose is commercially available from Aqualon Co. of Wilmington, Del. The chemical structure of MC is as follow:

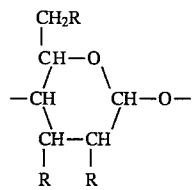

where R = OCH$_3$ where R=O CH$_3$

Figure 14:
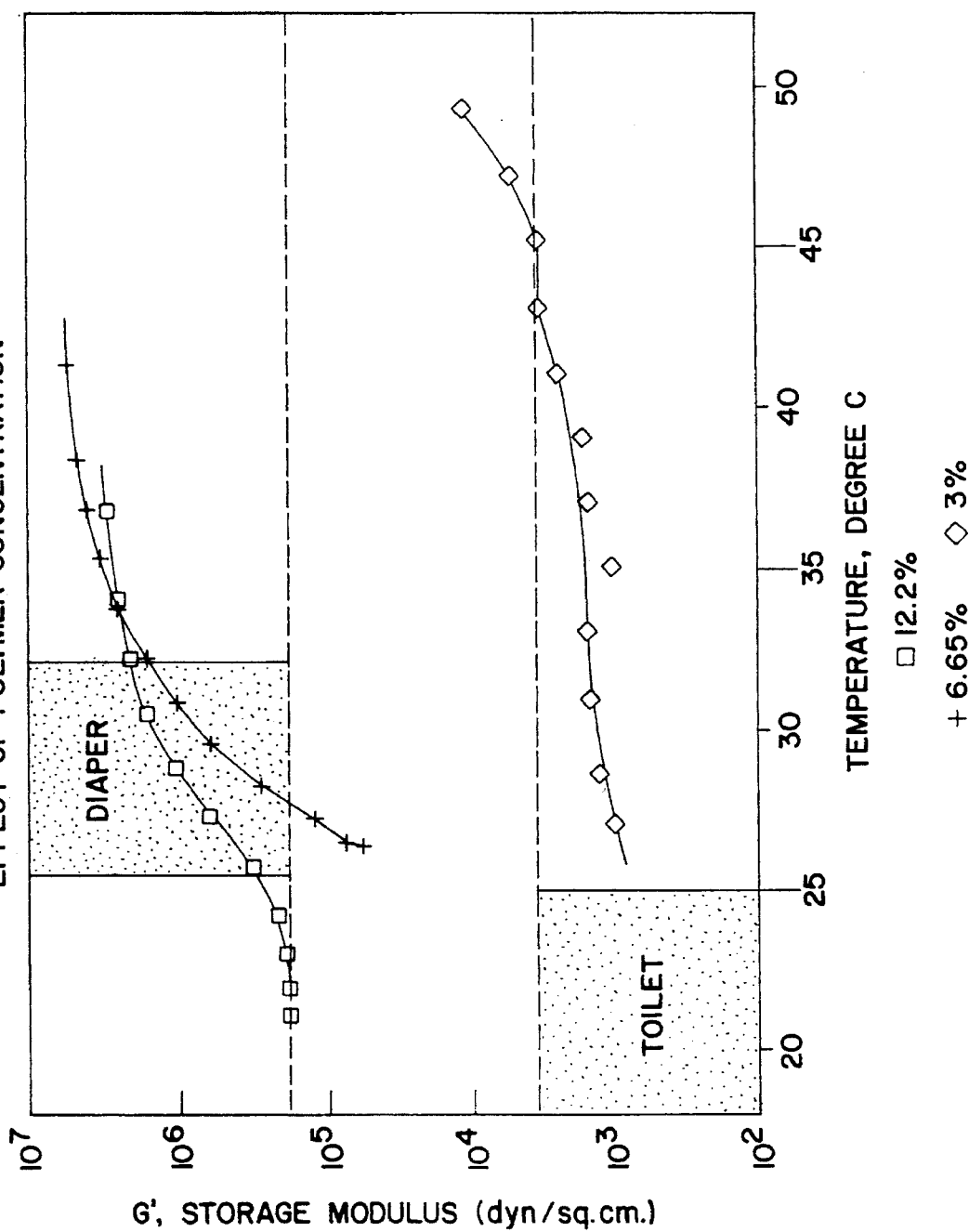
FIG. 14 is a graph of storage moduli (G') values as a function of temperature for various methyl cellulose polymer preparations.
Figure 15:
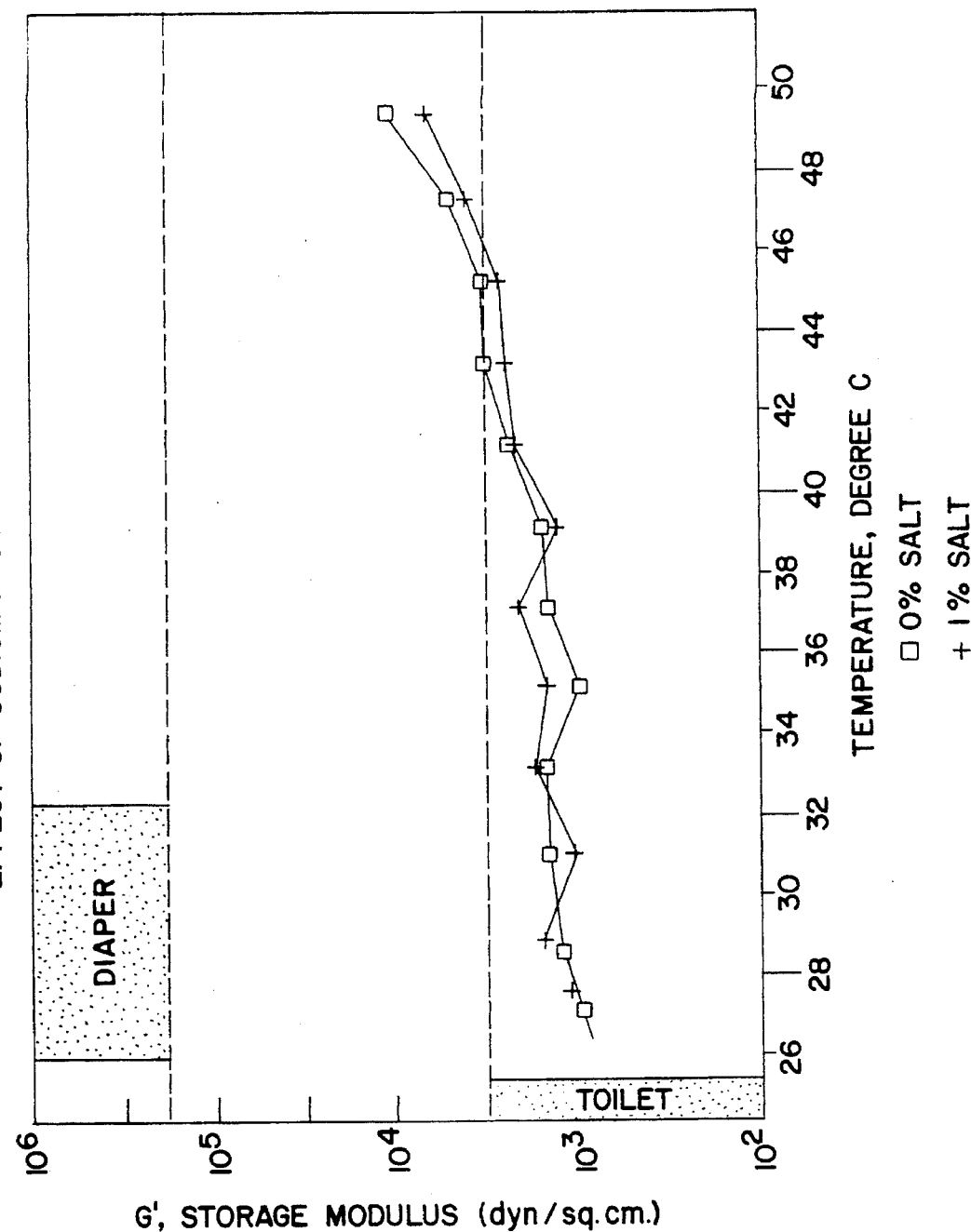
FIG. 15 is a graph of storage moduli (G') values as a function of temperature for various methyl cellulose polymer preparations containing salt.

Methyl cellulose having a molecular weight of 86,000, supplied by Polysciences, Inc. of Warrington, Pa., was used to evaluate the effect of temperature on the value of G'. FIG. 14 shows a plot of G' values as a function of temperature for MC having different degrees of hydration. Methyl cellulose is capable of absorbing a large amount of water, as much as 35 grams water per gram of polymer (approximately 3 weight % (wt %) of the polymer concentration) and forms a soft hydrogel. At polymer concentrations of more than 6 wt %, it is a tough gel. FIG. 15 shows a plot of G' as a function of temperature for MC with and without sodium phosphate. It is apparent that sodium phosphate has little effect on the storage modulus of MC.

EXAMPLE 15

Polyethylene Oxide and Polyethylene Oxide Copolymers

Figure 16:
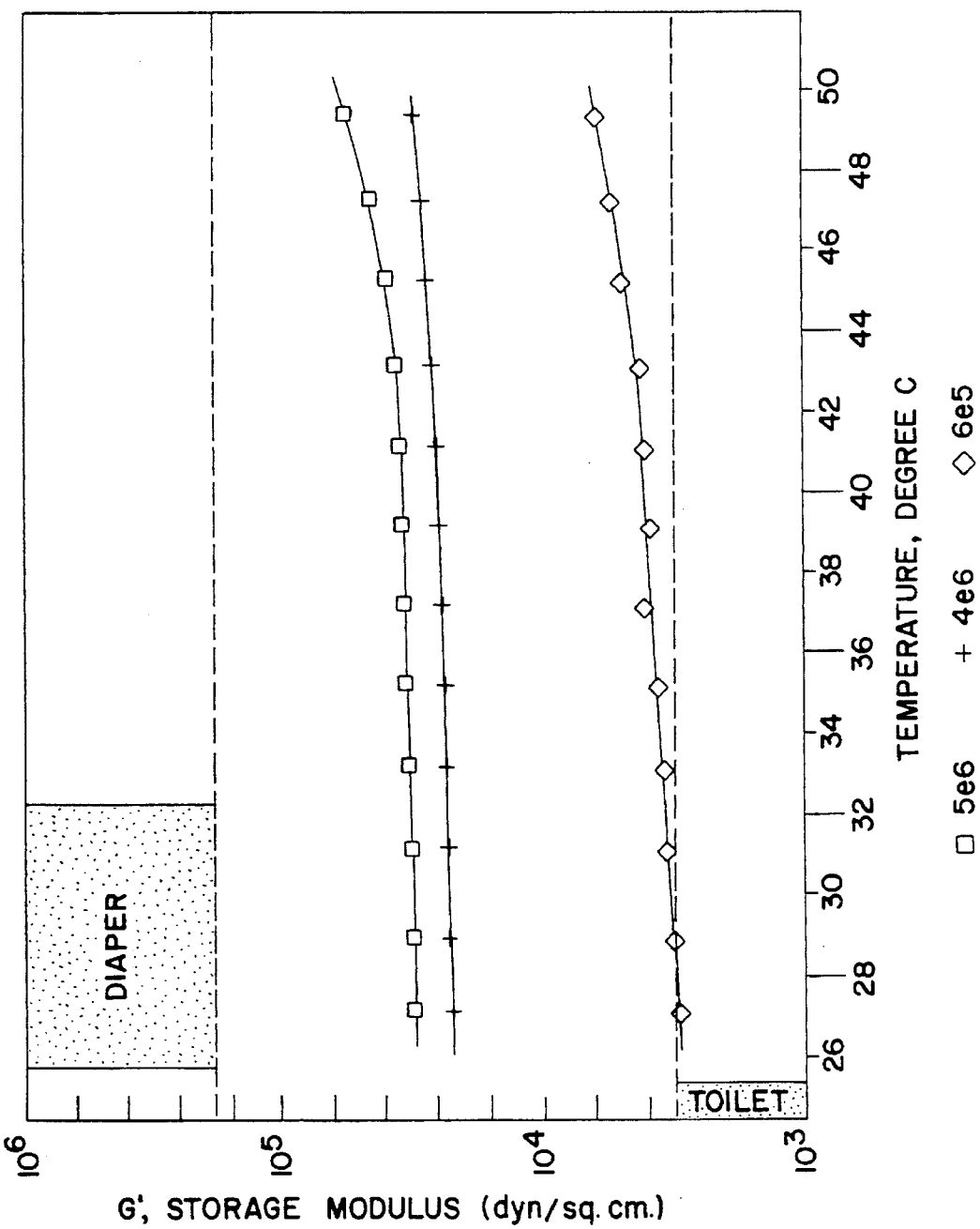
FIG. 16 is a graph of storage moduli (G') values as a function of temperature for various polyethylene oxide polymer preparations.

Polyethylene oxide has a cloud point of 101° C. The cloud point of polyethylene oxide is decreased by the presence of salts or by copolymerization with propylene oxide (See for example, "Effect of additives on solution properties of ethylene oxide propylene oxide statistical copolymers," by A. Louai, D. Sarazin, G. Pollet, J. Francois and F. Moreaux, Polymer, Vol. 32, pg. 713720 (1991) and "Some properties of polyethylene oxide in aqueous solution," by F. E. Bailey, Jr. and R. W. Callard, Journal of Applied Polymer Science, Vol. 1, pg. 56–62 (1959)). The chemical structures for PEO and PPO are given as follows:

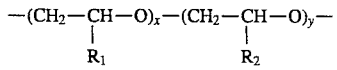

where $R_1=R_2=H$ ethylene oxide homopolymer $R_1=R_2=CH_3$ propylene oxide homopolymer $R_1=H, R_2=CH_3$ copolymer PEO polymers having different molecular weights (MW) were obtained from Union Carbide Corporation of New York, N.Y. POLYOX WSR N-10 has MW of 100,000. POLYOX WSR-205 has MW of 600,000. POLYOX WSR-301 has MW of 4,000,000. POLYOX Coagulant has MW of 5,000,000. FIG. 16 shows a plot of G' as a function of temperature for PEO having different molecular weights. It is apparent that the storage modulus for PEO increases with increasing molecular weight. Also, temperature has little effect on the storage modulus of PEO.

Figure 17:
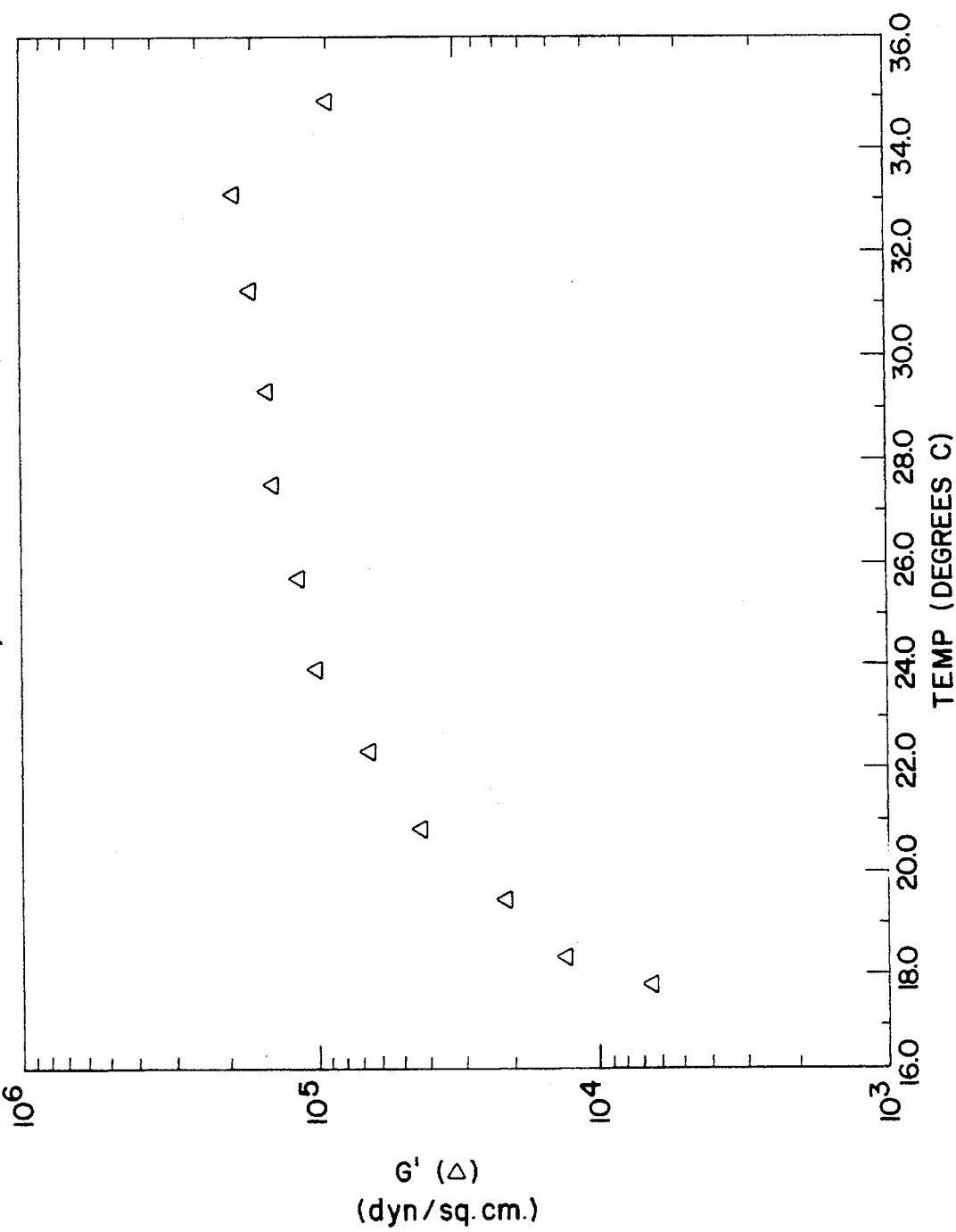
FIG. 17 is a graph of storage moduli (G') values as a function of temperature for ethylene oxide-propylene oxide copolymer.

The temperature-dependent thermoreversibility of PEO homopolymer can be modulated by the addition of a significant amount of salt, e.g. 0.3M to 0.4M sodium phosphate. Alternatively, the cloud point of PEO can be decreased by copolymerization with propylene oxide or butylene oxide, designated EOPO and EOBO copolymers, respectively. EOPO and EOBO copolymers are available from several chemical manufactures, such as Dow Chemical and Union Carbide. The EOPO polymer selected for testing for temperature-dependent thermoreversibility is a waxy solid containing 3 parts of ethylene oxide and 1 part of propylene oxide, has a molecular weight of 13,300, and was obtained from Polysciences, Inc. of Warrington, Pa. FIG. 17 shows a plot of G' values as a function of temperature for a sample having a polymer concentration of 17.8%. It is clear that the sample exhibits an increase in G' value at elevated temperatures.

The wet strength of the flushable composition is increased by blending a high strength polymer, such as polyolefin or high molecular weight PEO with the low molecular weight EOPO copolymer. Optionally, various salts can be blended into the composition. The low molecular weight EOPO copolymer constitutes the active temperature-dependent thermoreversible component, while the other polymer contributes strength to the composition.

EXAMPLE 16

Three pounds of precipitated calcium carbonate Socal 31 obtained from Specialty Minerals, Inc. (formerly Pfizer Co.) of Bethlehem, Pa. and 3 lbs. of polyethylene wax A-C 16 obtained from Allied Signal, Inc. of Morristown, N.J. were compounded using a laboratory scale attritor provided by Standridge Color Co. of Social Circle, Ga. The average particle size of the calcium carbonate is 0.07 micron. Five pounds of the PE wax/carbonate mixture was further mixed with 5 lbs. of Klucel LF from Aqualon Co. of Wilmington, Del. by using a paint mixer model 5400 supplied by Red Devil Equipment Co. of Union, N.J. The final mixture had a composition of Klucel/wax/carbonate of 50:25:25. The mixture was melt spun into polymeric filaments according to the process disclosed in U.S. Pat. No. 4,340,563, which is hereby incorporated herein in its entirety by reference.

EXAMPLE 17

A flushable article is provided wherein a backsheet is in superposed facing relation to a first side of an absorbent body, the absorbent body in turn is superposed in facing relation on a second side to a bodyside liner, and wherein one or more of the backsheet, absorbent body and bodyside liner are composed of a thermoreversible flushable polymer, wherein the polymer is insoluble or non-dispersible in body waste fluids at temperatures above approximately 25° C., and is soluble or dispersible in water at temperatures below approximately 23° C.

An absorbent article as described, for example, in U.S. Pat. No. 5,192,606, which is hereby incorporated herein in its entirety by reference, that has one or more flushable components is provided. The absorbent article includes a backsheet layer, an absorbent body, an optional liquid permeable intermediate transfer layer, and a body side liner. The backsheet generally is impervious to penetration by urine and other body wastes, and acts as an outer covering for the absorbent article. The absorbent body generally is composed of substantially hydrophilic material that is capable of absorbing liquid. The bodyside liner (also referred to as the topsheet) is a liquid permeable layer that comprises the surface of the article that will be in contact with the skin of the wearer of the article.

EXAMPLE 18

A partially flushable absorbent article as described in Example 17 is provided. The flushable absorbent article includes a flushable absorbent body. The absorbent body may be constructed using a mixture of pulp and methyl cellulose.

EXAMPLE 19

A partially flushable absorbent article as described in Example 17 is provided. The flushable absorbent article includes a flushable backsheet layer. The backsheet layer is constructed using a cast film composition of hydroxypropyl cellulose with 1% calcium carbonate or calcium phosphate.

EXAMPLE 20

A totally flushable absorbent article as described in Example 17 is provided. The flushable article can be flushed as a whole article in toilet bowl. Not all of the components of the article have to break apart and disperse prior to flushing because the article will continue to disintegrate in municipal or private sewage systems after flushing.

EXAMPLE 21

An absorbent article as described in U.S. Pat. No. 4,798,603 to Meyer et al., which is hereby incorporated herein in its entirety by reference, is constructed wherein one or more of the components of the absorbent article is a flushable component. Such flushable components may be made according to the foregoing Examples. Such an absorbent article comprises a liquid permeable transport layer located between a topsheet (bodyside liner) and a hydrophilic absorbent body, having an effective average pore size that is smaller than the pore size of the topsheet layer, and a backsheet.

EXAMPLE 22

An absorbent article as described, for example, in U.S. Pat. No. 5,192,606 and having one or more flushable components is provided. The absorbent article includes a backsheet layer, an absorbent body and a liquid permeable intermediate transfer layer, and body side liner. Also, the absorbent article includes two containment flaps that are connected to the bodyside surface of the transfer layer. Suitable constructions and arrangements for containment flaps are described, for example, in U.S. Pat. No. 4,704,116 issued Nov. 3, 1987, to K. Enloe. The flushable components may be removed and flushed in toilet bowl. The flushable components may include, but are not limited to, a body side liner, a transfer layer, and containment flaps. These flushable components may be constructed using nonwoven fabrics as described in the foregoing Examples.

EXAMPLE 23

A partially flushable absorbent article as described in Example 22 is provided. The flushable components as described in Example 22 are constructed using flushable nonwoven fabrics.

EXAMPLE 24

A partially flushable absorbent article as described in Example 22 is provided. The flushable absorbent article includes a flushable absorbent body. The absorbent body is constructed using a mixture of pulp and methyl cellulose.

EXAMPLE 25

A totally flushable absorbent article as described in Example 22 may be provided. The flushable article can be flushed as a whole article in toilet bowl. All components of the article do not have to break-apart prior to flushing.

EXAMPLE 26

A partially flushable disposable training pant or incontinence garment as described in, for example, U.S. Pat. No. 4,938,757 and U.S. Pat. No. 4,940,464, both of which are hereby incorporated herein in their entirety by reference, are provided. The flushable training pant includes an absorbent assembly comprising a liquid-impervious outer cover, a liquid-pervious liner, and an absorbent medium therebetween. A pair of stretchable side panels are joined to the absorbent assembly to form a waist opening and a pair of leg openings. The said liner may be flushable and may be constructed using material as described in Example 4.

EXAMPLE 27

A flushable tampon applicator as described in, for example, U.S. Pat. No. 4,676,773 and U.S. Pat. No. 5,002,526, both of which are hereby incorporated herein in their entirety by reference, is provided. The standard construction for a tampon applicator is a pair of telescoping tubes, the outer tube carrying the tampon's absorbent material (the tampon's 'pledget') and the inner tube serving as a plunger for dispensing the pledget. The applicators are molded to include a grip ring and a petal-shaped forward end which aids in the insertion of the device and in retaining and protecting the pledget while it is in the outer tube. Flushable applicators are constructed by injection molding a mixture of ethylene methacrylic acid copolymer, calcium phosphate salt, pigment, plasticizer and reinforcing substance such as polyethylene.

EXAMPLE 28

A flushable sanitary napkin as described in, for example, U.S. Pat. No. 4,944,735 and U.S. Pat. No. 5,032,121, both of which are hereby incorporated herein in their entirety by reference, is provided. The sanitary napkin consists of an absorbent body, a fluid permeable cover positioned adjacent to the absorbent body, e.g. superposed in facing relation to the absorbent body, and a fluid-impermeable baffle. The cover and baffle are sealed together to enclose the absorbent body. The sanitary napkin further includes a pair of elastic members affixed between the cover and the baffle. The cover is made flushable by using nonwoven fabric described in the foregoing Examples. The baffle may be made flushable by using a cast film of mixture containing polyethyl oxazoline, salt, polyethylene, plasticizer and pigment.

EXAMPLE 29

A flushable panty liner as described in, for example, U.S. Pat. No. 4,347,092, which is hereby incorporated herein in its entirety by reference, may be provided. The panty liner includes an absorbent body, a fluid permeable cover and a fluid impermeable baffle. The cover may be made flushable by using nonwoven fabric described in the foregoing Examples. The baffle may be made flushable by using a cast film of mixture containing polyethyl oxazoline, salt, polyethylene, plasticizer and pigment.

The above described invention will be more fully understood in view of the following embodiments. It is to be understood that the above-disclosed embodiments are merely illustrative and are not intended to limit the scope of the invention. On the contrary, other embodiments will become obvious to one skilled in the art in light of the disclosure of the present invention and all such obvious variations are contemplated within the scope of the appended claims.

What is claimed is:

1. A flushable composition comprising,
    a temperature sensitive water soluble polymer, in combination with means for altering the temperature at which the polymer is water soluble, the means comprising a salt admixed with the polymer in an amount sufficient to render the polymer reversibly water insoluble in the presence of body waste fluids having a temperature above approximately 25° C., but soluble or dispersible in the presence of normal tap water having a temperature below approximately 23° C.

2. The flushable composition of claim 1, wherein the composition has a storage modulus (G') value of greater than approximately $2 \times 10^5$ dyne/cm$^2$ when in contact with urine having a temperature in a range of 25° C. to 37° C., and a G' value of less than approximately $5 \times 10^3$ dyne/cm$^2$ when in contact with water having a temperature below 23° C.

3. The flushable composition of claim 1, wherein the temperature sensitive water soluble polymer is selected from the group consisting of polymethacrylic acid, polymethacrylic acid copolymers, polyvinyl alcohol having a degree of hydrolysis of less than 75%, polyethyl oxazoline, polyvinyl methyl ether, polyvinyl pyrrolidone/vinyl acetate copolymers, hydroxypropyl cellulose, hydroxypropyl methyl cellulose, methyl cellulose, ethyl hydroxyethyl cellulose, methyl ether starch, poly (n-isopropyl acrylamide), poly N-vinyl caprolactam, polyvinyl methyl oxazolidone, polyvinyl methyl oxazolidimone, poly(2-isopropyl-2-oxazoline), poly (2,4-dimethyl-6-triazinyl ethylene), polyethylene oxide, and ethylene oxide-propylene oxide copolymer.

4. The flushable composition of claim 1, wherein the flushable composition comprises polyvinyl alcohol that has a degree of hydrolysis of less than 75% and a salt selected from the group consisting of sulfate salts, citrate salts, phosphate salts and chromate salts.

5. The flushable composition of claim 1, wherein the flushable composition comprises polyethyl oxazoline and a salt selected from the group consisting of phosphate salts, sulfate salts, carbonate salts, and halide salts.

6. The flushable composition of claim 1, wherein the flushable composition comprises hydroxypropyl cellulose and an inorganic salt.

7. A flushable article comprising, a backsheet in superposed facing relation to a first side of an absorbent body, the absorbent body superposed in facing relation on a second side to a bodyside liner, wherein one or more of the backsheet, absorbent body and bodyside liner are composed of the flushable composition of claim 1.

8. The flushable composition of claim 1, wherein the flushable composition comprises polyvinyl pyrrolidone copolymer and an inorganic salt.

9. The flushable composition of claim 8, wherein the inorganic salt is ammonium sulfate.

10. A flushable article comprising,
the flushable composition of claim 1, wherein the article is selected from the group consisting of infant care products, child care products, adult care products, feminine care products, wet wipes, medical care products, surgical products, packaging materials and household wipes.

11. The flushable article of claim 10, wherein the flushable composition has a storage modulus (G') value of greater than approximately $2 \times 10^5$ dyne/cm$^2$ when in contact with urine having a temperature in a range of 25° C. to 37° C., and a G' value of less than approximately $5 \times 10^3$ dyne/cm$^2$ when in contact with water having a temperature below 23° C.

12. The flushable article of claim 10, wherein the temperature sensitive water soluble polymer is selected from the group consisting of polymethacrylic acid, polymethacrylic acid copolymers, polyvinyl alcohol having a degree of hydrolysis of less than 75%, polyethyl oxazoline, polyvinyl methyl ether, polyvinyl pyrrolidone/vinyl acetate copolymers, hydroxypropyl cellulose, hydroxypropyl methyl cellulose, methyl cellulose, ethyl hydroxyethyl cellulose, methyl ether starch, poly (n-isopropyl acrylamide), poly N-vinyl caprolactam, polyvinyl methyl oxazolidone, polyvinyl methyl oxazolidimone, poly(2-isopropyl-2-oxazoline), poly (2,4-dimethyl-6-triazinyl ethylene), polyethylene oxide, and ethylene oxide-propylene oxide copolymer.

13. The flushable article of claim 9, wherein the flushable composition comprises polyvinyl alcohol that has a degree of hydrolysis of less than 75% and a salt selected from the group consisting of sulfate salts, citrate salts, phosphate salts and chromate salts.

14. The flushable article of claim 9, wherein the flushable composition comprises polyethyl oxazoline and a salt selected from the group consisting of phosphate salts, sulfate salts, carbonate salts and halide salts.

15. The flushable article of claim 10 wherein the temperature sensitive water soluble polymer is selected from the group consisting of polymethacrylic acid copolymers, polyvinyl alcohol having a degree of hydrolysis of less than 75%, polyethyl oxazoline, polyvinyl methyl ether, polyvinyl pyrrolidone/vinyl acetate copolymers, and methyl cellulose.

16. The flushable article of claim 10 wherein said flushable composition is in the form of a fibrous nonwoven fabric.

17. The flushable article of claim 9, wherein the flushable composition comprises hydroxypropyl cellulose and an inorganic salt.

18. The flushable article of claim 10, wherein the flushable composition comprises polyvinyl pyrrolidone copolymer and an inorganic salt.

19. The flushable article of claim 18, wherein the inorganic salt is ammonium sulfate.

\* \* \* \* \*

UNITED STATES PATENT AND TRADEMARK OFFICE

CERTIFICATION OF CORRECTION

PATENT NO. : 5,509,913

DATED : April 23, 1996

INVENTOR(S): Richard S. Yeo

It is certified that error appears in the above-identified patent and that said Letters Patent is hereby corrected as shown below:

```
Title page,
Item [75]    Inventor: "Richard S. Yeo", should read --Richard S. C. Yeo--;
Item [56]    Line 25, Other Publications: "93,303509/37", should read --92-303509/37--;

Item [56]    Line 17, "by Heymann", should read --by E. Heymann--

Item [56]    Line 24, "Frans", should read --Franks--.
```

Signed and Sealed this

Thirty-first Day of December, 1996

Attest:

BRUCE LEHMAN

*Attesting Officer*    *Commissioner of Patents and Trademarks*